United States Patent
Dacko et al.

(10) Patent No.: US 11,274,167 B2
(45) Date of Patent: *Mar. 15, 2022

(54) CARBAMATE FUNCTIONAL MONOMERS AND POLYMERS AND USE THEREOF

(71) Applicant: PRC-DeSoto International, Inc., Sylmar, CA (US)

(72) Inventors: Christopher A. Dacko, Pittsburgh, PA (US); Hongying Zhou, Allison Park, PA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/454,723

(22) Filed: Jun. 27, 2019

(65) Prior Publication Data

US 2020/0407471 A1    Dec. 31, 2020

(51) Int. Cl.
| | |
|---|---|
| *C08F 20/36* | (2006.01) |
| *C07C 271/22* | (2006.01) |
| *C07C 275/16* | (2006.01) |
| *C08J 5/18* | (2006.01) |
| *C09D 133/14* | (2006.01) |

(52) U.S. Cl.
CPC ............ *C08F 20/36* (2013.01); *C07C 271/22* (2013.01); *C07C 275/16* (2013.01); *C08J 5/18* (2013.01); *C09D 133/14* (2013.01); *C08J 2333/14* (2013.01)

(58) Field of Classification Search
None
See application file for complete search history.

(56) References Cited

U.S. PATENT DOCUMENTS

| | | |
|---|---|---|
| 3,479,328 A | 11/1969 | Nordstrom |
| 3,937,679 A | 2/1976 | Bosso et al. |
| 3,947,338 A | 3/1976 | Jerabek et al. |
| 3,984,299 A | 10/1976 | Jerabek |
| 4,104,100 A | 8/1978 | Anders et al. |
| 4,151,143 A | 4/1979 | Blank et al. |
| 4,397,970 A | 8/1983 | Campbell et al. |
| 4,617,343 A | 10/1986 | Walker et al. |
| 4,692,484 A | 9/1987 | Roberts |
| 4,692,503 A | 9/1987 | Das et al. |
| 4,793,867 A | 12/1988 | Charles et al. |
| 4,801,628 A | 1/1989 | Ashing et al. |
| 4,812,215 A | 3/1989 | Karabin et al. |
| 4,886,852 A | 12/1989 | Numa |
| 4,957,952 A | 9/1990 | Sekmakas et al. |
| 4,968,399 A | 11/1990 | Tsuchiya et al. |
| 5,066,564 A | 11/1991 | Zertani et al. |
| 5,356,669 A | 10/1994 | Rehfuss et al. |
| 5,384,367 A | 1/1995 | Swarup et al. |

(Continued)

FOREIGN PATENT DOCUMENTS

| | | |
|---|---|---|
| CN | 106883344 | 6/2017 |
| CN | 109666119 | 4/2019 |

(Continued)

OTHER PUBLICATIONS

Jang et al., Synthesis and properties of rotaxane-cross-linked polymers using a double-stranded gamma]-CD-based inclusion complex as a supramolecular cross-linker; Polymer; Jan. 26, 2017; pp. 379-385; vol. 128; Elsevier Ltd. (Year: 2017).*

Keumhee Jang et al., "Synthesis and properties of rotaxane-cross-linked polymers using a double-stranded [gamma]-CD-based inclusion complex as a supramolecular cross-linker"; Polymer; Jan. 26, 2017; pp. 379-385; vol. 128; Elsevier Ltd.

Hongping Xiang et al., "Effect of soft chain length and generation number on properties of flexible hyperbranched polyurethane acrylate and its UV-cured film"; Progress in Organic Coatings; Nov. 2, 2017; pp. 216-222; vol. 114; Elsevier B.V.; the Netherlands.

Rhodia, "Sipomer PAM-100 and PAM-200 Sipomer WAM"; Aug. 31, 2003; retrieved from the Internet on Sep. 28, 2020.

(Continued)

Primary Examiner — Satya B Sastri
(74) Attorney, Agent, or Firm — Charles M. Yeomans

(57) ABSTRACT

The present invention is directed to a compound of formula I,

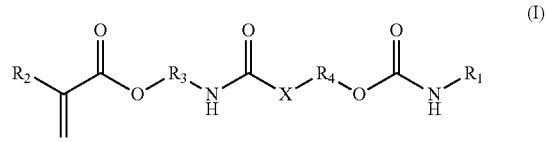

wherein $R_1$ comprises hydrogen, an alkyl group, or an aryl group; $R_2$ comprises hydrogen or a methyl group; $R_3$ comprises a divalent organic group; $R_4$ comprises a divalent organic group; and X comprises oxygen, NH, or $N(R_5)$, wherein $R_5$ comprises a monovalent organic group. The present invention is also directed towards polymers comprising a pendant carbamate-functional moiety comprising the structure:

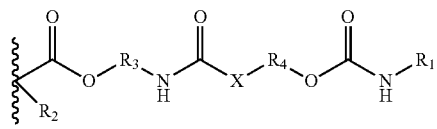

wherein $R_1$ comprises hydrogen, an alkyl group, or an aryl group; $R_2$ comprises hydrogen or a methyl group; $R_3$ comprises a divalent organic group; $R_4$ comprises a divalent organic group; and X comprises oxygen, NH, or $N(R_5)$ wherein $R_5$ comprises a monovalent organic group. The present invention is also directed to methods of preparing such compounds and polymers, compositions comprising such polymers, and coatings produced from such compositions.

22 Claims, No Drawings

(56) References Cited

U.S. PATENT DOCUMENTS

| | | | |
|---|---|---|---|
| 5,389,704 A | 2/1995 | Yabu | |
| 5,525,666 A | 6/1996 | Hoenel et al. | |
| 5,588,989 A | 12/1996 | Vonk et al. | |
| 5,605,965 A * | 2/1997 | Rehfuss | C08G 18/3831 |
| | | | 525/100 |
| 5,635,049 A | 6/1997 | Mysliwczyk et al. | |
| 5,814,410 A | 9/1998 | Singer et al. | |
| 5,936,026 A | 8/1999 | Huybrechts et al. | |
| 6,136,927 A | 10/2000 | Swarup et al. | |
| 6,165,338 A * | 12/2000 | December | C25D 13/22 |
| | | | 204/506 |
| 6,214,188 B1 | 4/2001 | December | |
| 6,380,323 B1 | 4/2002 | December | |
| 6,509,411 B1 | 1/2003 | Fieberg et al. | |
| 6,875,800 B2 | 4/2005 | Vanier et al. | |
| 6,894,086 B2 | 5/2005 | Munro et al. | |
| 6,984,674 B2 | 1/2006 | Gray et al. | |
| 7,622,241 B2 | 11/2009 | Munnelly | |
| 7,671,170 B2 | 3/2010 | Gonzalez et al. | |
| 7,749,368 B2 | 7/2010 | McMurdie et al. | |
| 8,148,451 B2 | 4/2012 | Fenn et al. | |
| 8,153,344 B2 | 4/2012 | Faler et al. | |
| 8,323,470 B2 | 12/2012 | Valko et al. | |
| 8,354,471 B2 | 1/2013 | Chouai et al. | |
| 8,673,091 B2 | 3/2014 | Mcmillen et al. | |
| 8,702,943 B2 | 4/2014 | December et al. | |
| 9,181,628 B2 | 11/2015 | Valko et al. | |
| 9,505,937 B2 | 11/2016 | Hsu et al. | |
| 9,951,169 B2 | 4/2018 | Yang et al. | |
| 10,947,408 B2 | 3/2021 | Dacko et al. | |
| 2002/0068176 A1 | 6/2002 | Yokoyama et al. | |
| 2003/0127332 A1 | 7/2003 | Bremser et al. | |
| 2006/0135651 A1 | 6/2006 | Nakane et al. | |
| 2006/0252900 A1 * | 11/2006 | Bowman | C07D 339/08 |
| | | | 526/318 |
| 2009/0045071 A1 | 2/2009 | Valko et al. | |
| 2009/0054583 A1 | 2/2009 | Fringant et al. | |
| 2010/0048836 A1 | 2/2010 | Gonzalez et al. | |
| 2010/0255301 A1 | 10/2010 | Moeller et al. | |
| 2012/0121910 A1 | 5/2012 | Colton et al. | |
| 2013/0065057 A1 | 3/2013 | Valko et al. | |
| 2013/0065985 A1 | 3/2013 | Anderson et al. | |
| 2013/0090443 A1 | 4/2013 | Musa | |
| 2013/0172472 A1 | 7/2013 | Greyson et al. | |
| 2015/0197665 A1 | 7/2015 | Hsieh et al. | |
| 2017/0313899 A1 | 11/2017 | Xu et al. | |
| 2017/0363957 A1 * | 12/2017 | Roelle | G03F 7/0046 |
| 2018/0002558 A1 | 1/2018 | Tomko et al. | |
| 2018/0016376 A1 | 1/2018 | Belowich et al. | |
| 2018/0051112 A1 | 2/2018 | Liu et al. | |
| 2019/0051905 A1 * | 2/2019 | Zhamu | H01M 4/483 |
| 2021/0071031 A1 * | 3/2021 | Miao | C08G 18/246 |

FOREIGN PATENT DOCUMENTS

| | | |
|---|---|---|
| DE | 19917235 | 10/2001 |
| EP | 0300612 | 1/1989 |
| EP | 2749596 | 7/2014 |
| JP | S63212586 | 9/1988 |
| JP | H06336564 | 12/1995 |
| JP | 2008169308 | 7/2008 |
| KR | 20140112987 | 9/2014 |
| WO | 0037560 | 6/2000 |
| WO | 0039190 | 7/2000 |
| WO | 2001044392 | 6/2001 |
| WO | 2001048097 | 7/2001 |
| WO | 03054048 | 7/2003 |
| WO | 2007118024 | 10/2007 |
| WO | 2015156032 | 10/2015 |

OTHER PUBLICATIONS

Anonymous, "2-Acrylamido-2-methylpropane sulfonic acid", Wikipedia; Oct. 2, 2018; retrieved from the Internet on Oct. 16, 2020.

Faler, U.S. Appl. No. 10/876,031, filed Jun. 24, 2004, for "Aqueous Dispersions of Microparticles Having a Nanoparticulate Phase and Coating Compositions Containing the Same", now abandoned, 94 pages.

* cited by examiner

CARBAMATE FUNCTIONAL MONOMERS AND POLYMERS AND USE THEREOF

FIELD OF THE INVENTION

The present invention is directed towards a compound having formula I as described herein, a method of making said compound, polymers, methods of making such polymers, and compositions comprising such polymers.

BACKGROUND INFORMATION

Unsaturated monomers are useful for synthesizing a variety of polymers. The polymers can have various properties based upon the mixture of monomers that make up the composition of the polymer. Functionalized unsaturated monomers allow for the production of polymers having the functional groups. Polymers comprising the residue of unsaturated monomers are useful in a variety of industries including, but not limited to, coatings. Novel unsaturated monomers and polymers that provide new and/or improved properties to compositions comprising the same are desired.

SUMMARY OF THE INVENTION

Disclosed herein is a compound of formula I,

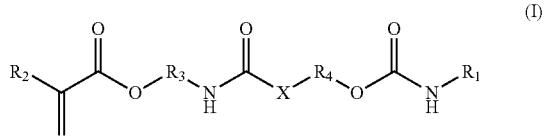

wherein $R_1$ comprises hydrogen, an alkyl group, or an aryl group; $R_2$ comprises hydrogen or a methyl group; $R_3$ comprises a divalent organic group; $R_4$ comprises a divalent organic group; and X comprises oxygen, NH, or $N(R_5)$, wherein $R_5$ comprises a monovalent organic group.

Also disclosed herein is a polymer comprising a pendant carbamate-functional moiety comprising the structure:

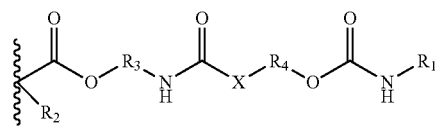

wherein $R_1$ comprises hydrogen, an alkyl group, or an aryl group; $R_2$ comprises hydrogen or a methyl group; $R_3$ comprises a divalent organic group; $R_4$ comprises a divalent organic group; and X comprises oxygen, NH, or $N(R_5)$ wherein $R_5$ comprises a monovalent organic group.

Further disclosed herein is an aqueous resinous dispersion or curable film-forming composition comprising the polymer of the present invention.

Also disclosed is an aqueous resinous dispersion comprising the polymer of the present invention.

Further disclosed is a coating comprising the polymer of the present invention.

Also disclosed is a method of preparing a compound of formula I, the method comprising the step of reacting an isocyanato functional unsaturated monomer of formula II with a hydroxyl functional, carbamate functional monomer according to formula III,

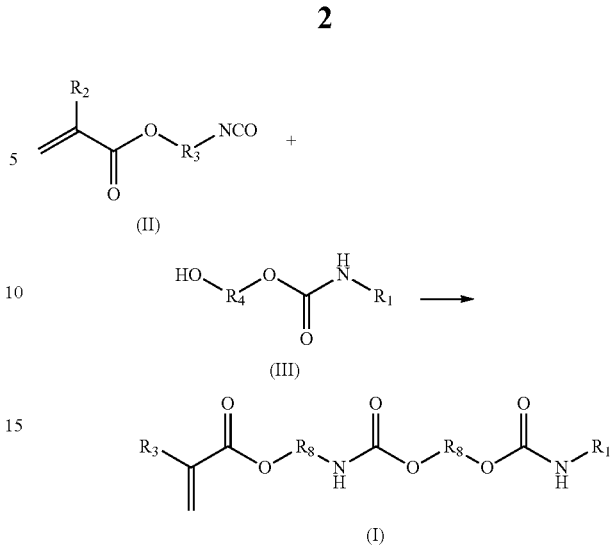

wherein $R_1$ comprises hydrogen, an alkyl group, or an aryl group; $R_2$ comprises hydrogen or a methyl group; $R_3$ comprises a divalent organic group; and $R_4$ comprises a divalent organic group.

Further disclosed is a method of preparing a compound of formula I, the method comprising the steps of (1) reacting an isocyanato functional unsaturated compound of formula II with a dihydroxy alkyl amine compound of formula IV to form a reaction product,

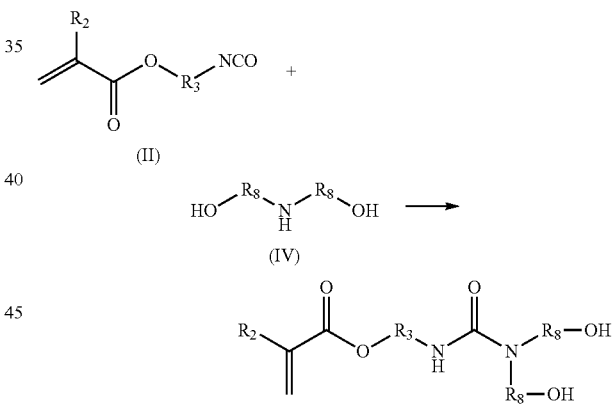

and (2) further reacting the reaction product with a carbamate ester according to formula V,

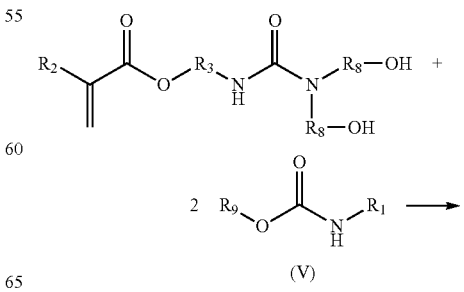

-continued

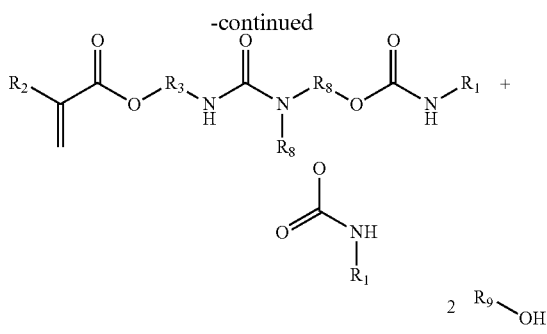

wherein $R_1$ comprises hydrogen, an alkyl group, or an aryl group; $R_2$ comprises hydrogen or a methyl group; $R_3$ comprises a divalent organic group; each $R_8$ independently comprises a divalent organic group; and $R_9$ comprises a monovalent organic group.

DETAILED DESCRIPTION OF THE INVENTION

As stated above, the present invention is directed to a compound of formula I,

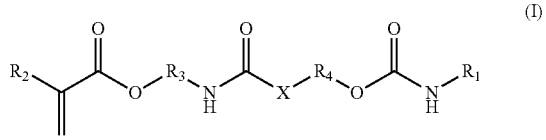

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_4$ comprises, consists essentially of, or consists of a divalent organic group; and X comprises, consists essentially of, or consists of oxygen, NH, or $N(R_5)$ wherein $R_5$ comprises, consists essentially of, or consists of a monovalent organic group. The divalent organic group may comprise, for example, a substituted or unsubstituted alkylene group, arylene group, or a combination thereof. The monovalent organic group of $R_5$ may comprise, for example, a substituted or unsubstituted alkyl group, aryl group, or a combination thereof, and the monovalent organic group may terminate in a carbamate functional group.

As used herein, a "divalent organic group" may comprise a divalent, substituted or unsubstituted organic group including an alkylene group, a cycloalkylene group, an aryl group, a cycloarylene group, or combinations thereof.

The divalent alkylene group of $R_3$ and $R_4$ may each independently comprise any alkylene group such as, for example, a $C_1$ to $C_{50}$ alkylene group, including, for example, methylene, ethylene, propylene, isopropylene, butylene, pentylene, hexylene, heptylene, and the like. The substituted divalent alkylene group of $R_3$ and $R_4$ may each independently comprise at least one ester group, carbamate ester group, ether group, or a combination thereof. For example, the divalent organic group of $R_3$ and $R_4$ may each independently comprise an ether substituted divalent alkylene group such as polyethylene glycol, polypropylene glycol, or a combination thereof. The divalent organic groups of $R_3$ and/or $R_4$ may be free of a cycloalkylene group. The divalent organic groups of $R_3$ and/or $R_4$ may be free of a carbamate ester group.

As used herein, the term "carbamate functional group" refers to a functional group according to the formula $R_xOC(=O)N(H)(R_y)$, wherein $R_x$ comprises an organic group and $R_y$ comprises hydrogen or an organic group.

The compound of formula I may comprise the structure:

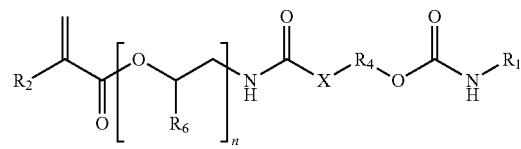

wherein $R_1$ comprises, consists essentially of, or consists of hydrogen, an alkyl group, or an aryl group; $R_2$ comprises, consists essentially of, or consists of hydrogen or a methyl group; $R_4$ comprises, consists essentially of, or consists of a divalent organic group; $R_6$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and n is a positive integer from 1 to 100.

The compound of formula I may comprise the structure:

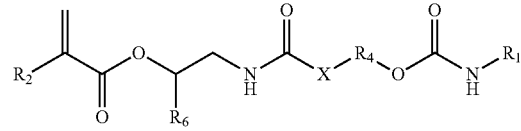

wherein $R_1$ comprises, consists essentially of, or consists of hydrogen, an alkyl group, or an aryl group; $R_2$ comprises, consists essentially of, or consists of hydrogen or a methyl group; $R_4$ comprises, consists essentially of, or consists of a divalent organic group; $R_6$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

The compound of formula I may comprise the structure:

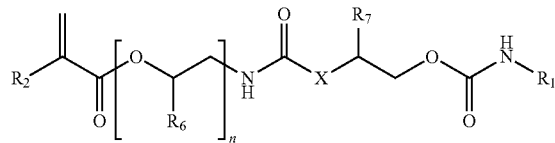

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and n is a positive integer from 1 to 100.

The compound of formula I may comprise the structure:

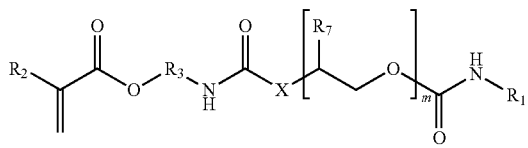

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and m is a positive integer from 1 to 100.

The compound of formula I may comprise the structure:

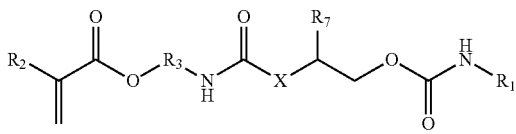

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_7$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

The compound of formula I may comprise the structure:

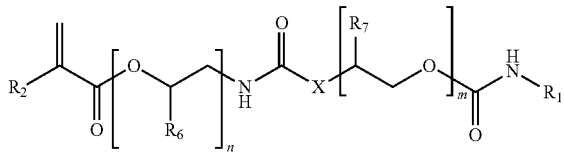

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; m is a positive integer from 1 to 100; and n is a positive integer from 1 to 100.

The compound of formula I may comprise the structure:

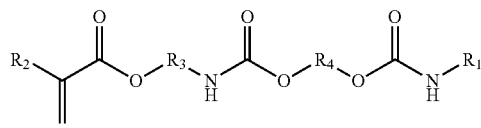

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and $R_4$ comprises, consists essentially of, or consists of a divalent organic group.

The compound of formula I may comprise the structure:

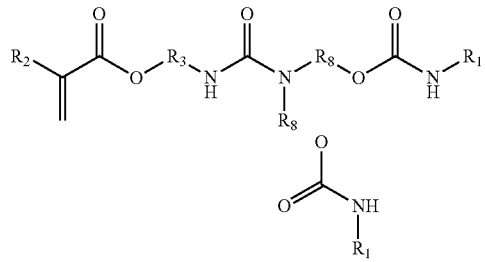

wherein each $R_1$ independently comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and each $R_8$ independently comprises, consists essentially of, or consists of a divalent organic group.

The compound of formula I may comprise the structure:

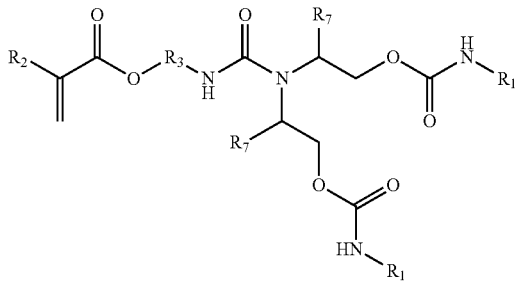

wherein each $R_1$ independently comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and each $R_7$ independently comprises, consists essentially of, or consists of hydrogen or a methyl group.

The compound of formula I may comprise the structure:

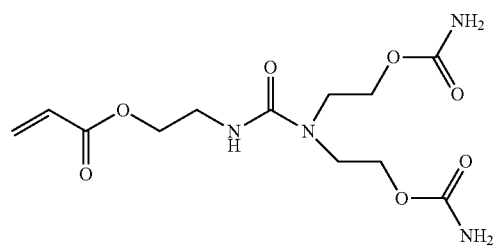 [SMILES: C=CC(=O)OCCNC(=O)N(CCOC(N)=O)CCOC(N)=O]

The compound of formula I may comprise the structure:

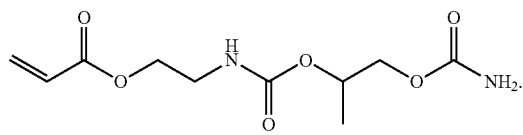 [SMILES: C=CC(=O)OCCNC(=O)OC(C)COC(N)=O]

The present invention is also directed to methods of preparing the compound of formula I.

A method of preparing the compound of formula I wherein X comprises oxygen may comprise the step of reacting an isocyanato functional unsaturated compound of formula II with a hydroxyl functional, carbamate functional compound according to formula III,

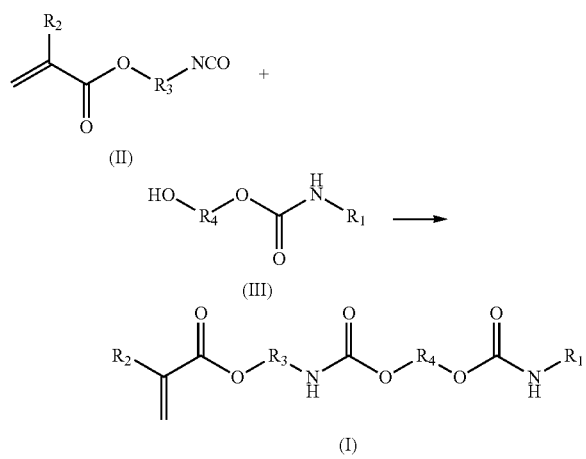

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and $R_4$ comprises, consists essentially of, or consists of a divalent organic group.

A method of preparing a compound of formula I wherein X comprises $N(R_5)$ may comprise the steps of (1) reacting an isocyanato functional unsaturated compound of formula II with a dihydroxy alkyl amine compound of formula IV to form a reaction product,

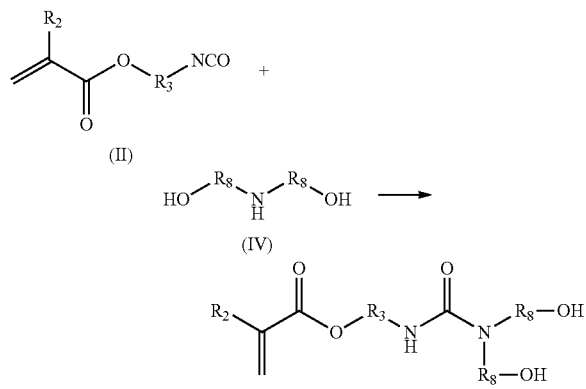

and (2) further reacting the reaction product with a carbamate ester according to formula V,

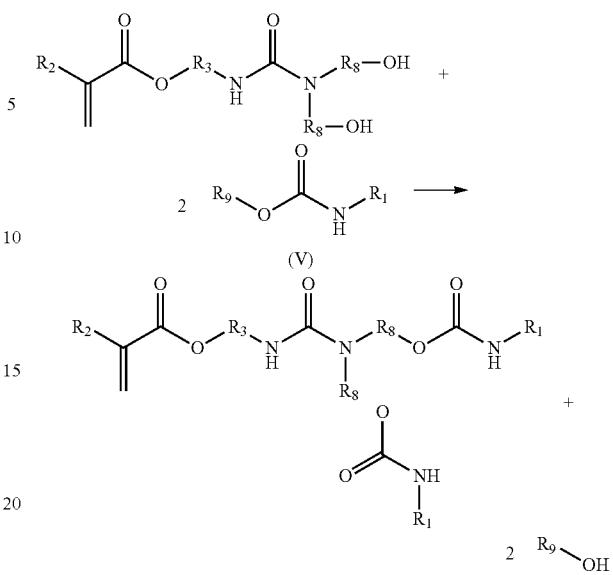

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; each $R_8$ independently comprises, consists essentially of, or consists of a divalent organic group; and $R_9$ comprises, consists essentially of, or consists of a monovalent organic group, such as a $C_1$ to $C_4$ alkyl group.

The present invention is also directed to a polymer comprising a pendant carbamate-functional moiety comprising the structure:

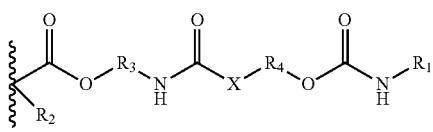

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_4$ comprises, consists essentially of, or consists of a divalent organic group; and X comprises, consists essentially of, or consists of oxygen, NH, or $N(R_5)$ wherein $R_5$ comprises, consists essentially of, or consists of a monovalent organic group. As used herein, unless indicated otherwise, the polymer backbone as depicted in structures is represented by a wavy line.

The polymer may comprise the residue of the compound of formula I such that the polymer is derived from, and comprises constitutional units comprising the residue of one or more carbamate functional, ethylenically unsaturated monomers according to formula I.

Alternatively, an intermediate polymer may comprise the residue of the compound of formula II such that the polymer is derived from, and comprises constitutional units comprising the residue of one or more isocyanato functional unsaturated monomers according to formula II to form an intermediate polymer, and the intermediate polymer may then be further reacted in a second step with a hydroxyl functional, carbamate functional compound according to formula III to form the polymer comprising a pendant carbamate-functional moiety.

The polymer may comprise an addition polymer. As used herein, the term "addition polymer" refers to a polymer at least partially or wholly derived from ethylenically unsaturated monomers. As used herein, the term "unsaturated" refers to the presence of at least one double bond that could be "saturated" by addition of $H_2$. As understood by one skilled in the art, ethylenically unsaturated groups of the monomers react during an addition polymerization reaction to form a growing polymeric chain of monomers with the residue of the unsaturated group of each monomer bonded along the chain by carbon-carbon bonds to form the polymer backbone and the remainder of each of the monomers form a pendant moiety or group. Accordingly, the polymer backbone generally comprises repeating units of ($-CH_2-C(R_2)(R_x)-$), wherein $R_2$ comprises hydrogen or a methyl group; and $R_x$ comprises a pendant moiety that may be equivalent to the portion of the monomer bound to the original unsaturated group (which may be further modified to be carbamate functional, as discussed above).

A non-limiting example of the polymer comprising a pendant carbamate-functional moiety comprises the following structure:

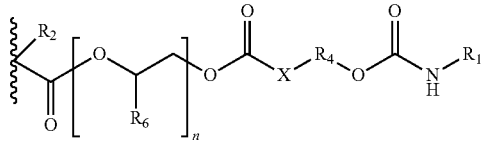

wherein $R_1$ comprises, consists essentially of, or consists of hydrogen, an alkyl group, or an aryl group; $R_2$ comprises, consists essentially of, or consists of hydrogen or a methyl group; $R_4$ comprises, consists essentially of, or consists of a divalent organic group; $R_6$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and n is a positive integer from 1 to 100.

A non-limiting example of the polymer comprising a pendant carbamate-functional moiety comprises the following structure:

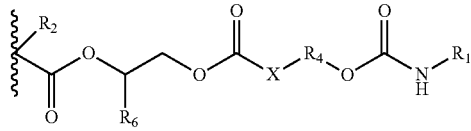

wherein $R_1$ comprises, consists essentially of, or consists of hydrogen, an alkyl group, or an aryl group; $R_2$ comprises, consists essentially of, or consists of hydrogen or a methyl group; $R_4$ comprises, consists essentially of, or consists of a divalent organic group; $R_6$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

A non-limiting example of the polymer comprising a pendant carbamate-functional moiety comprises the following structure:

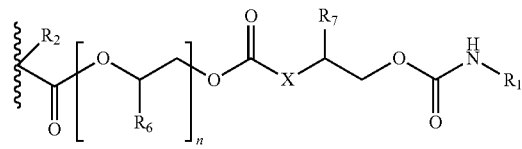

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and n is a positive integer from 1 to 100.

A non-limiting example of the polymer comprising a pendant carbamate-functional moiety comprises the following structure:

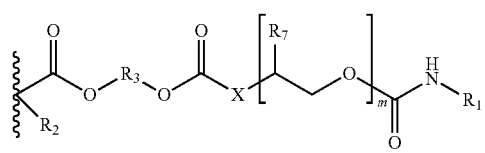

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and m is a positive integer from 1 to 100.

A non-limiting example of the polymer comprising a pendant carbamate-functional moiety comprises the following structure:

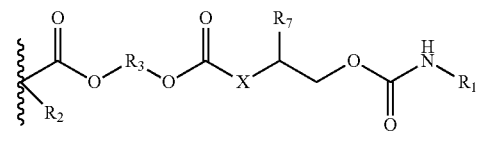

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_7$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

A non-limiting example of the polymer comprising a pendant carbamate-functional moiety comprises the following structure:

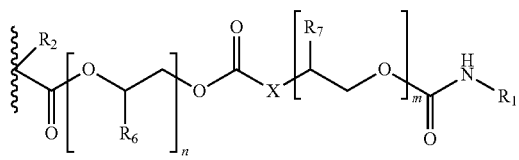

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; m is a positive integer from 1 to 100; and n is a positive integer from 1 to 100.

A non-limiting example of the polymer comprising a pendant carbamate-functional moiety comprises the following structure:

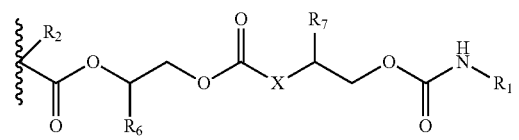

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

A non-limiting example of the polymer comprising a pendant carbamate-functional moiety wherein the moiety comprises a carbamate ester comprises the following structure:

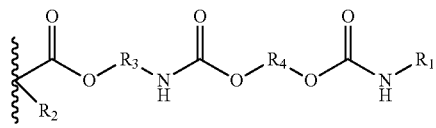

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and $R_4$ comprises, consists essentially of, or consists of a divalent organic group.

A non-limiting example of the polymer comprising a pendant carbamate-functional moiety wherein the moiety comprises a carbamate ester comprises the following structure:

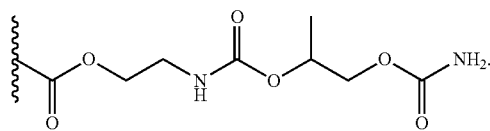 [SMILES: *C(=O)OCCNC(=O)OC(C)COC(N)=O]

A non-limiting example of the polymer comprising a pendant carbamate-functional moiety wherein the moiety comprises a urea group comprises the following structure:

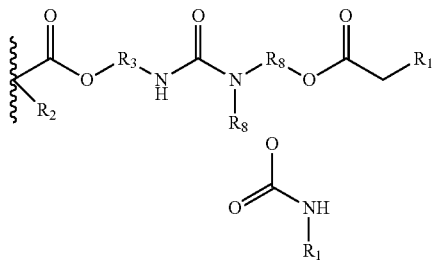

wherein each $R_1$ independently comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and each $R_8$ independently comprises, consists essentially of, or consists of a divalent organic group.

A non-limiting example of the polymer comprising a pendant carbamate-functional moiety wherein the moiety comprises a urea group comprises the following structure:

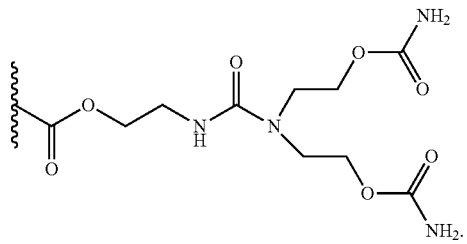 [SMILES: *C(=O)OCCNC(=O)N(CCOC(N)=O)CCOC(N)=O]

The polymer comprising a pendant carbamate-functional moiety may optionally further comprise constitutional units comprising the residue of other ethylenically unsaturated monomers. When other ethylenically unsaturated monomers are used to produce the polymer, constitutional units comprising the pendant carbamate-functional moiety (such as those comprising residue of the compound of formula I) may comprise, for example, at least 1% by weight, such as at least 10% by weight, such as at least 30% by weight, such as at least 40% by weight, and may comprise no more than 95% by weight, such as no more than 75% by weight, such as no more than 65% by weight, such as no more than 60% by weight, based on the total weight of the polymer. The constitutional units comprising the pendant carbamate-functional moiety may comprise, for example, 1% to 95% by weight, such as 10% to 75% by weight, such as 30% to 65% by weight, such as 40% to 60% by weight, based on the total weight of the polymer. The polymer may be derived from a reaction mixture of polymerizable monomers comprising the compound of formula I in an amount of, for example, 1% to 95% by weight, 10% to 75% by weight, such as 30% to 65% by weight, such as 40% to 60% by weight, based on the total weight of polymerizable monomers used in the reaction mixture to make the polymer. The polymer may also be derived from a reaction mixture of polymerizable monomers comprising the isocyanato functional unsaturated monomers according to formula II in an amount of, for example, 1% to 95% by theoretical combined weight of the isocyanato functional unsaturated monomers according to formula II and hydroxyl functional, carbamate functional compound according to formula III after post-reaction, 10% to 75% by combined weight, such as 30% to 65% by combined weight, such as 40% to 60% by combined weight, based on the total weight of polymerizable monomers used in the reaction mixture to make the polymer.

Non-limiting examples of other ethylenically unsaturated monomers include (meth)acrylic acids, alkyl esters of (meth)acrylic acid, hydroxyalkyl esters, sulfonic acid functional ethylenically unsaturated monomers, phosphorous acid functional ethylenically unsaturated monomers, ethylenically unsaturated monomers comprising other functional groups such as, for example, epoxide, hydroxyl, thiol, amino, urea, and/or amide functional groups, vinyl aromatic monomers.

As noted above, the other ethylenically unsaturated monomers may comprise functional groups in addition to the ethylenically unsaturated group(s), and the polymer optionally may further comprise these other functional groups when such monomers are used including, for example, epoxide, hydroxyl, thiol, amino, urea, amide, sulfonic acid, phosphorous acid, and/or carboxylic acid functional groups. Alternatively, the polymer may be substantially free, essentially free, or completely free of any or all of these functional groups. As used herein, the term "substantially free", "essentially free" or "completely free" with respect to the presence of a functional group means that the functional group is present, if at all, in an amount of 3% or less, 0.1% or less, or 0.00%, respectively, the percentage based upon the total number of the functional group relative to the total number of functional groups.

The polymer optionally may be derived from and further comprise constitutional units comprising the residue of one or more alkyl esters of (meth)acrylic acid. Non-limiting examples of the alkyl esters of (meth)acrylic acid include those that contain from 1 to 18 carbon atoms in the alkyl group, such as 1 to 3 or 4 to 18. Non-limiting examples of alkyl esters of (meth)acrylic acid include methyl (meth) acrylate, ethyl (meth)acrylate, propyl (meth)acrylate, and the like.

The constitutional units comprising the residue of the alkyl esters of (meth)acrylic acid, if present, may comprise 10% to 90% by weight, such as 15% to 50% by weight, such as 20% to 40% by weight, based on the total weight of the polymer. The polymer may be derived from a reaction mixture of polymerizable monomers comprising alkyl esters of (meth)acrylic acid in an amount of 10% to 90% by weight, such as 15% to 50% by weight, such as 20% to 40% by weight, based on the total weight of polymerizable monomers used in the reaction mixture.

The polymer optionally may be derived from and further comprise constitutional units comprising the residue of one or more alpha, beta-ethylenically unsaturated carboxylic acids. Non-limiting examples of alpha, beta-ethylenically unsaturated carboxylic acids include those containing up to 10 carbon atoms such as acrylic acid and methacrylic acid. Non-limiting examples of other unsaturated acids are alpha, beta-ethylenically unsaturated dicarboxylic acids such as maleic acid or its anhydride, fumaric acid and itaconic acid. Also, the half esters of these dicarboxylic acids may be employed.

The constitutional units comprising the residue of the alpha, beta-ethylenically unsaturated carboxylic acids, if present, may comprise, for example, 1% to 30% by weight, such as 2% to 20% by weight, such as 3% to 15% by weight, based on the total weight of the polymer. The polymer may be derived from a reaction mixture comprising alpha, beta-ethylenically unsaturated carboxylic acids, if present, in an amount of, for example, 1% to 30% by weight, such as 2% to 20% by weight, such as 3% to 15% by weight, based on the total weight of polymerizable monomers used in the reaction mixture.

The polymer optionally may be derived from and further comprise constitutional units comprising the residue of one or more vinyl aromatic monomers. Non-limiting examples of vinyl aromatic monomers include styrene, alpha-methyl styrene, alpha-chlorostyrene and vinyl toluene.

The constitutional units comprising the residue of the vinyl aromatic monomers, if present, may comprise, for example, 1% to 30% by weight, such as 5% to 25% by weight, such as 10% to 20% by weight, based on the total weight of the polymer. The polymer may be derived from a reaction mixture comprising vinyl aromatic monomers, if present, in an amount of, for example, 1% to 30% by weight, such as 5% to 25% by weight, such as 10% to 20% by weight, based on the total weight of polymerizable monomers used in the reaction mixture.

The polymer optionally may be derived from and further comprise constitutional units comprising the residue of one or more hydroxyalkyl esters. Non-limiting examples of hydroxyalkyl esters include hydroxyethyl (meth)acrylate and hydroxypropyl (meth)acrylate.

The constitutional units comprising the residue of the hydroxyalkyl esters, if present, may comprise, for example, 1% to 30% by weight, such as 2% to 20% by weight, such as 3% to 15% by weight, based on the total weight of the polymer. The polymer may be derived from a reaction mixture comprising hydroxyalkyl esters, if present, in an amount of, for example, 1% to 30% by weight, such as 2% to 20% by weight, such as 3% to 15% by weight, based on the total weight of polymerizable monomers used in the reaction mixture, if present.

The polymer optionally may be derived from and further comprise constitutional units comprising the residue of one or more phosphorous acid functional, ethylenically unsaturated monomers. Such monomers comprise at least one phosphorous acid functional group and at least one ethylenically unsaturated group. The phosphorous acid group may comprise a phosphonic acid group, or a phosphinic acid group, and a combination of monomers comprising different phosphorous acids may be used. The phosphorous acid functional, ethylenically unsaturated monomers may comprise an organophosphonic acid, ethylenically unsaturated monomer, and may be according to the general structure:

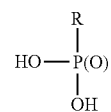

wherein R comprises an organyl group comprising at least one ethylenically unsaturated group. As used herein, the term "organyl group" refers to a monovalent organic group that may include alkyl, cycloalkyl, aryl, cycloaryl groups, or a combination thereof. The organyl group R may comprise further substitution in addition to the at least one ethylenically unsaturated group. The phosphorous acid functional, ethylenically unsaturated monomers may comprise an organophosphinic acid, ethylenically unsaturated monomer, and may be according to the structure:

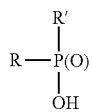

wherein R comprises an organyl group comprising at least one ethylenically unsaturated group; and R' comprises hydrogen, an organyl group, or a phosphoester group. The organyl group of R or R' may each independently comprise, for example, an alkyl, cycloalkyl, aryl, or cycloaryl group, or a combination thereof (e.g., aliphatic/aromatic, etc.). Examples of such organyl groups are those having a total of 1-30, such as 6-18 carbons. R and R' may comprise further substitution in addition to the at least one ethylenically unsaturated group of organyl group R. For example, the R group may terminate in an oxygen atom bound to the phosphorous atom such that the R group comprises a phosphoester group.

A non-limiting example of a phosphorous acid functional, ethylenically unsaturated monomer includes a monomer according to the structure:

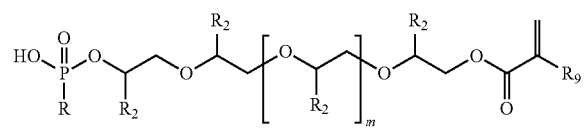

wherein R comprises, consists essentially of, or consists of hydrogen, hydroxyl, an alkyl radical, an aryl radical, or a phosphoester group; each $R_2$ independently comprises, consists essentially of, or consists of hydrogen, methyl, or a $C_2$ to $C_6$ alkyl group; $R_9$ comprises, consists essentially of, or consists of hydrogen, methyl, or a $C_2$ to $C_6$ alkyl group; and m is an integer from 1 to 100.

When used, the phosphorous acid group is present within a moiety of the polymer. The moiety comprising the phosphorous acid group may comprise the structure:

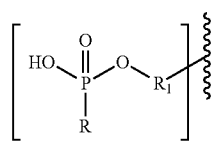

wherein R comprises, consists essentially of, or consists of hydrogen, hydroxyl, an alkyl radical, an aryl radical, or a phosphoester group, and $R_1$ comprises, consists essentially of, or consists of an organic linking group terminating in a carbon atom that is covalently bonded to a carbon atom present in the polymer backbone. The organic linking group comprises at least one carbon atom, and may comprise additional functional groups, such as, for example, one or more ether functional groups, among other functional groups, and at least a portion of the organic linking group may comprise a polyether if at least two ether groups are present. The organic linking group may comprise an organic chain, and the organic chain may terminate in a carbon atom on either side of the chain. The organic linking group, $R_1$, may be free of carboxylic acid. A non-limiting example of the moiety comprising the phosphorous acid group may be the moiety comprising the structure:

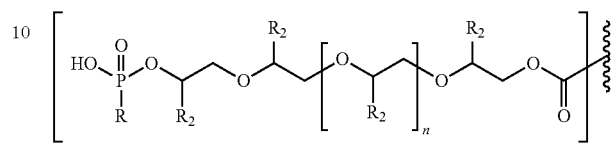

wherein R comprises, consists essentially of, or consists of hydrogen, hydroxyl, an alkyl radical, an aryl radical, or a phosphoester group; each $R_2$ independently comprises, consists essentially of, or consists of hydrogen, methyl, or a $C_2$ to $C_6$ alkyl group; and n is an integer from 1 to 100.

The constitutional units comprising the residue of the phosphorous acid functional, ethylenically unsaturated monomer, if present, may comprise, for example, 0.1% to 10% by weight, such as 0.5% to 5% by weight, such as 1% to 4% by weight, based on the total weight of the polymer. The polymer may be derived from a reaction mixture of polymerizable monomers comprising a phosphorous acid functional, ethylenically unsaturated monomer, if present, in an amount of, for example, 0.1% to 10% by weight, such as 0.5% to 5% by weight, such as 1% to 4% by weight, based on the total weight of polymerizable monomers used in the reaction mixture. If present, the polymer may have a theoretical phosphorous acid equivalent weight of, for example, 500 to 150,000 g/equivalent, such as 1,000 to 50,000 g/equivalent, such as 5,000 to 25,000 g/equivalent, based on the total solids weight of the polymer.

The polymer optionally may be derived from and comprise constitutional units comprising the residue of one or more sulfonic acid functional ethylenically unsaturated monomers. Such monomers comprise at least one sulfonic acid functional group and at least one ethylenically unsaturated group. The sulfonic acid functional ethylenically unsaturated monomers may be according to the general structure:

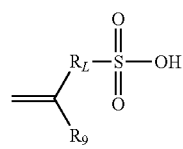

wherein $R_L$ comprises, consists essentially of, or consists of an organic linking group and $R_9$ comprises hydrogen or a methyl group. A non-limiting example of a sulfonic acid functional ethylenically unsaturated monomer includes 2-acrylamide-2-methylpropane sulfonic acid (AMPS) having the structure:

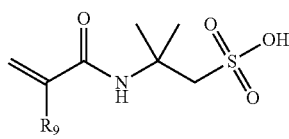

wherein $R_9$ comprises hydrogen or a methyl group.

When used, the sulfonic acid group is present within a moiety of the polymer. The moiety comprising the sulfonic acid group may comprise the structure:

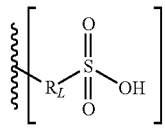

wherein $R_L$ is optional and comprises, consists essentially of, or consists of an organic linking group that binds the sulfonic acid group or salt thereof to the polymer backbone. The organic linking group represented by $R_L$ may comprise an alkylene group, an arylene group, a cycloalkylene group, a cycloarylene group, or combinations thereof, and may be substituted or unsubstituted, including substitution with further sulfonic acid groups or salts thereof. The organic linking group represented by $R_L$ may bind the moiety to the polymer backbone through a carbon-carbon bond. The organic linking group may be substituted or unsubstituted. For example, a specific non-limiting example of a moiety comprising sulfonic acid includes the moiety according to the structure:

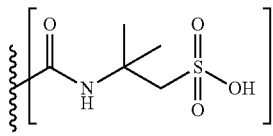

The constitutional units comprising the residue of the sulfonic acid functional ethylenically unsaturated monomers, if present, may comprise, for example, 0.1% to 10% by weight, such as 0.5% to 5% by weight, such as 1% to 4% by weight, based on the total weight of the polymer. The polymer may be derived from a reaction mixture comprising sulfonic acid functional ethylenically unsaturated monomers, if present, in an amount of, for example, 0.1% to 10% by weight, such as 0.5% to 5% by weight, such as 1% to 4% by weight, based on the total weight of polymerizable monomers used in the reaction mixture. If present, the polymer may have a theoretical sulfonic acid equivalent weight of 2,000 g/equivalent to 200,000 g/equivalent, such as 5,000 g/equivalent to 100,000 g/equivalent, such as 10,000 g/equivalent to 50,000 g/equivalent, based on the total solids weight of the polymer.

The polymer optionally may be derived from and comprise constitutional units comprising the residue of one or more ethylenically unsaturated monomers comprising a heterocyclic group. Non-limiting examples of ethylenically unsaturated monomers comprising a heterocyclic group include epoxy functional ethylenically unsaturated monomers, such as glycidyl (meth)acrylate, as well as vinyl pyrrolidone, vinyl pyridine, and vinyl caprolactam, among others.

The constitutional units comprising the residue of the ethylenically unsaturated monomers comprising a heterocyclic group, if present, may comprise, for example, 1% to 40% by weight, such as 5% to 30% by weight, 10% to 20% by weight, based on the total weight of the polymer. The polymer may be derived from a reaction mixture comprising the ethylenically unsaturated monomers comprising a heterocyclic group, if present, in an amount of, for example, 1% to 40% by weight, such as 5% to 30% by weight, 10% to 20% by weight, based on the total weight of polymerizable monomers used in the reaction mixture.

The polymer optionally may be derived from and comprise constitutional units comprising the residue of one or more self-crosslinking monomers. As used herein, the term "self-crosslinking monomer" refers to monomers that incorporate functional groups that may react with other functional groups present on the polymer, such as the carbamate functional groups or other optional functional groups. Non-limiting examples of self-crosslinking monomers include N-alkoxymethyl (meth)acrylamide monomers such as N-butoxymethyl (meth)acrylamide and N-isopropoxymethyl (meth)acrylamide, as well as self-crosslinking monomers containing blocked isocyanate groups, such as isocyanatoethyl (meth)acrylate in which the isocyanato group is reacted ("blocked") with a compound that unblocks at curing temperature. Examples of suitable blocking agents include epsilon-caprolactone, methylethyl ketoxime, butyl lactamide, and butyl glycolamide.

The constitutional units comprising the residue of the self-crosslinking monomers, if present, may comprise, for example, 0.5% to 30% by weight, such as 1% to 20% by weight, 2% to 10% by weight, based on the total weight of the polymer. The polymer may be derived from a reaction mixture comprising sulfonic acid functional ethylenically unsaturated monomers, if present, in an amount of, for example, 0.5% to 30% by weight, such as 1% to 20% by weight, 2% to 10% by weight, based on the total weight of polymerizable monomers used in the reaction mixture.

The polymer may have a theoretical carbamate functional group equivalent weight of, for example, at least 240 g/equivalent, such as at least 300 g/equivalent, such as 400 g/equivalent, and may be no more than 5,000 g/equivalent, such as no more than 2,500 g/equivalent, such as no more than 1,000 g/equivalent, based on the total solids weight of the polymer. The polymer may have a theoretical carbamate functional group equivalent weight of, for example, 240 to 5,000 g/equivalent, such as 300 to 2,500 g/equivalent, such as 400 to 1,000 g/equivalent, based on the total solids weight of the polymer.

The z-average molecular weight ($M_z$) of the polymer may be, for example, at least 20,000 g/mol, such as at least 40,000 g/mol, such as at least 60,000 g/mol, and may be no more than 500,000 g/mol, such as no more than 250,000 g/mol, such as no more than 150,000 g/mol. The z-average molecular weight of the polymer may be, for example, in a range from 20,000 to 500,000 g/mol, 40,000 to 250,000 g/mol, such as 60,000 to 150,000 g/mol. As used herein, the term "z-average molecular weight" or "(M)" means the z-average molecular weight ($M_z$) as determined by gel permeation chromatography (GPC) using polystyrene standards for calibration. The GPC determination can be performed using a Waters 2695 separation module with a Waters 410 differential refractometer (RI detector), linear polystyrene standards having molecular weights of from 580 Da to 365,000 Da, dimethylformamide (DMF) with 0.05M lithium bromide (LiBr) as the eluent at a flow rate of 0.5 mL/min, and one Shodex Asahipak GF-510 HQ column (300×7.5 mm, 5 µm) for separation.

The polymer may alternatively have a weight average ($M_w$) of, for example, at least 1,000 g/mol, such as at least 1,500 g/mol, such as at least 2,000 g/mol, and may be no more than 20,000 g/mol, such as no more than 15,000 g/mol, such as no more than 12,000 g/mol. The polymer may have a weight average ($M_x$) molecular weight of, for example, from 1,000 to 20,000 g/mol, such as 1,500 to 15,000 g/mol, such as 2,000 to 12,000 g/mol. As used herein, the term "weight average molecular weight" or "($M_w$)" means the weight average molecular weight ($M_w$) as determined by gel permeation chromatography (GPC) using polystyrene standards for calibration. The GPC determination can be performed the same as for measuring the z-average molecular weight.

The present invention is also directed to a method of making the polymer described above, the method comprising polymerizing a mixture of ethylenically unsaturated monomers comprising (i) the compound according to formula I; and optionally (ii) at least one other ethylenically unsaturated monomer.

The polymer may be prepared by conventional free radical initiated solution polymerization techniques in which the polymerizable monomers are dissolved in an organic medium and polymerized in the presence of a free radical initiator until conversion is complete. Alternatively, the polymer may be prepared by conventional emulsion polymerization techniques in which the monomers are emulsified in water with an optional emulsifier and polymerized in the presence of a free radical initiator until conversion is complete.

Examples of free radical initiators are those which are soluble in the mixture of monomers such as azobisisobutyronitrile, azobis(alpha, gamma-methylvaleronitrile), tertiary-butyl perbenzoate, tertiary-butyl peracetate, benzoyl peroxide, ditertiary-butyl peroxide and tertiary amyl peroxy 2-ethylhexyl carbonate. The free radical initiator may be present in an amount of 0.01 to 6 parts by weight, per 100 parts of resin solids. Any percentages of resin solids included herein do not include the weight of the free radical initiator.

Optionally, a chain transfer agent which is soluble in the mixture of monomers such as alkyl mercaptans, for example, tertiary-dodecyl mercaptan; ketones such as methyl ethyl ketone, chlorohydrocarbons such as chloroform can be used. A chain transfer agent provides control over the molecular weight to give products having required viscosity for various applications.

To prepare the polymer, the solvent may be first heated to reflux and the mixture of polymerizable monomers containing the free radical initiator may be added slowly to the refluxing solvent. The reaction mixture is then held at polymerizing temperatures so as to reduce the free monomer content, such as to below 1.0 percent or below 0.5 percent, based on the total weight of the mixture of polymerizable monomers.

The present invention is also directed to a method of making the polymer described above, the method comprising the steps of (1) polymerizing a mixture of ethylenically unsaturated monomers comprising (i) the isocyanato functional unsaturated monomers according to formula II; and optionally (ii) at least one other ethylenically unsaturated monomer to form an intermediate polymer; and (2) further reacting the intermediate polymer with a hydroxyl functional, carbamate functional compound according to formula III to form the polymer.

The first step of the method may be performed as described above.

The second step of the method may be performed by adding the hydroxyl-functional, carbamate-functional species to the isocyanato-functional intermediate polymer in the presence of a catalyst. The temperature of this reaction may be from 60-80° C. and completion of reaction may be evaluated by IR spectroscopy for disappearance of the isocyanato peak at about 2200-2300 cm-1) indicating all of the isocyanato groups were consumed. A non-limiting example of an isocyanato-functional intermediate polymer reacted with a hydroxyl functional, carbamate functional compound may be as follows:

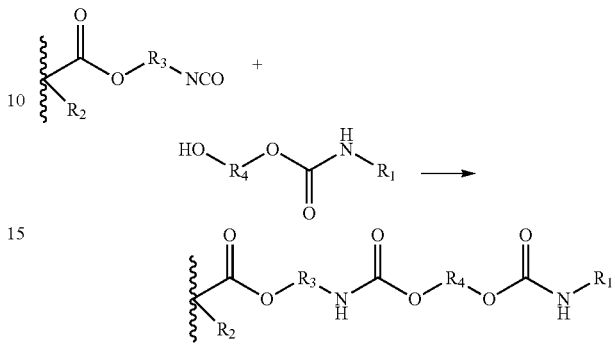

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and $R_4$ comprises, consists essentially of, or consists of a divalent organic group.

The present invention is also directed to a curable film-forming composition comprising the polymer. As used herein, the term "film-forming" with respect to the composition refers to a composition that includes components that can form a self-supporting continuous film on at least a horizontal surface of a substrate upon removal of any diluents or carriers present in the composition or upon curing of the composition at ambient or elevated temperature.

The curable film-forming coating composition may optionally further comprise a liquid medium, and the coating composition may be in the form of a liquid coating composition. As used herein, the term "liquid medium" refers to a liquid material that serves as a carrier for the components of the curable film-forming coating composition that may be substantially or completely removed from the composition upon drying and/or curing. The liquid medium may comprise an organic solvent. The organic solvent may comprise any suitable organic solvent known in the art. When solvent is used as a liquid medium (i.e., diluent), the coating composition may be a solvent borne coating composition. Solvent may be present in an amount such that the liquid medium is a non-aqueous liquid medium. As used herein, the term "non-aqueous medium" refers to a liquid medium comprising less than 50 weight % water, based on the total weight of the liquid medium. Such non-aqueous liquid mediums can comprise less than 40 weight % water, or less than 30 weight % water, or less than 20 weight % water, or less than 10 weight % water, or less than 5% water, or less than 1% water, based on the total weight of the liquid medium. The solvents that make up at least or more than 50 weight % of the liquid medium include organic solvents. Non-limiting examples of suitable organic solvents include polar organic solvents e.g. protic organic solvents such as glycols, glycol ether alcohols, alcohols; and volatile ketones, glycol diethers, esters, and diesters. Other non-limiting examples of organic solvents include aromatic and aliphatic hydrocarbons.

The liquid medium may be present in the curable film-forming coating composition in an amount of 5-85% by weight, such as 5-50% by weight, such as 5-40% by weight, such as 10-40% by weight, such as 25% to 60% by weight, such as 30% to 50% by weight, based on the total weight of the coating composition.

According to the present invention, the curable film-forming coating composition may be substantially free of a liquid medium, such as an organic solvent, wherein the coating composition is in the form of a co-reactable solid in particulate form, i.e., a powder coating composition.

According to the present invention, the curable film-forming coating composition may be substantially free of a liquid medium, such as an organic solvent, wherein the coating composition is in the form of a 100% solids composition. As used herein, a "100% solids composition" is a composition in a liquid form that comprises the materials that make up the coating film without a diluent, such as an organic solvent.

According to the present invention, the polymer may be dispersed in a dispersing medium comprising water. The polymer may be, prior to or during dispersion in a dispersing medium comprising water, at least partially neutralized by, for example, treating with a base to form a water-dispersible anionic salt group-containing polymer. As used herein, the term "water-dispersible" means that a material is adapted to be solubilized, dispersed, and/or emulsified in water. As used herein, the term "anionic salt group-containing polymer" refers to a polymer comprising at least partially neutralized anionic functional groups, such as, for example, phosphorous acid groups, that impart a negative charge to the resin. Non-limiting examples of suitable bases include both organic and inorganic bases. Illustrative examples of suitable bases are ammonia, monoalkylamines, dialkylamines, or trialkylamines such as ethylamine, propylamine, dimethylamine, dibutylamine and cyclohexylamine; monoalkanolamine, dialkanolamine or trialkanolamine such as ethanolamine, diethanolamine, triethanolamine, propanolamine, isopropanolamine, diisopropanolamine, dimethylethanolamine and diethylethanolamine; morpholines, e.g., N-methylmorpholine or N-ethylmorpholine. The percent of neutralization can be selected such that the polymer is made water-dispersible and electrophoretic. One or more of such bases may be added to the polymer in an amount sufficient to theoretically neutralize the polymer from, for example, 20 to 200 percent, such as 40 to 150 percent, such as 60 to 120 percent of theoretical neutralization.

The present invention is also directed to an aqueous resinous dispersion comprising the polymer comprising a pendant carbamate-functional moiety dispersed in the aqueous resinous dispersion, as described above. The aqueous resinous dispersion comprises a dispersion of the polymer in a continuous phase of an aqueous medium. The aqueous medium comprises greater than 50% by weight water, based on the total weight of the aqueous medium. For example, the aqueous medium may comprise at least 80% by weight water, based on the total weight of the aqueous medium. The aqueous medium may further comprise one or more organic solvents. Examples of suitable organic solvents include oxygenated organic solvents, such as monoalkyl ethers of ethylene glycol, diethylene glycol, propylene glycol, and dipropylene glycol which contain from 1 to 10 carbon atoms in the alkyl group, such as the monoethyl and monobutyl ethers of these glycols. Examples of other at least partially water-miscible solvents include alcohols such as ethanol, isopropanol, butanol and diacetone alcohol. If used, the amount of organic solvent present in the aqueous dispersion may be less than 20% by weight, such as less than 10% by weight, such as less than 5% by weight, with the % by weight being based on the total weight of the aqueous medium. Any other optional ingredients may be present in the dispersed resinous phase, the continuous phase, a third phase that is neither the resinous phase nor the continuous phase, or in a combination of the resinous phase, continuous phase and/or third phase, and may be either solubilized, dispersed, or a combination thereof.

According to the present invention, the aqueous resinous dispersion or curable film-forming composition of the present invention may optionally further comprise a curing agent. The curing agent may comprise at least two functional groups that react with the functional groups of the polymer to cure the coating composition to form a coating. As noted above, functional groups of the polymer include at least carbamate functional groups and may optionally further include phosphorous acid groups, sulfonic acid groups, and/or other active hydrogen functional groups, such as hydroxyl, thiol, and carboxylic acid groups. As used herein, the term "cure", "cured" or similar terms, as used in connection with the aqueous resinous dispersion or curable film-forming composition described herein, means that at least a portion of the components that form the aqueous resinous dispersion or curable film-forming composition are crosslinked to form a thermoset coating and is measured according to the Double Acetone Test Method. Additionally, curing of the aqueous resinous dispersion or curable film-forming composition refers to subjecting said composition to curing conditions (e.g., elevated temperature) leading to the reaction of the reactive functional groups of the components of the aqueous resinous dispersion or curable film-forming composition, and resulting in the crosslinking of the components of the composition and formation of an at least partially cured coating. Examples of suitable curing agents include at least partially blocked polyisocyanates, aminoplast resins and phenoplast resins, such as phenolformaldehyde condensates including allyl ether derivatives thereof. Non-limiting examples of such curing agents are described in U.S. patent application Ser. No. 16/019,590 at paragraphs [0049] to [0058], the cited portion of which is incorporated herein by reference.

The curing agent may be present in the aqueous resinous dispersion or curable film-forming composition in an amount of 10% to 50% by weight, such as 20% to 45% by weight, such as 25% to 40% by weight, based on the total weight of the resin solids of the aqueous resinous dispersion or curable film-forming composition.

According to the present invention, the aqueous resinous dispersions or curable film-forming compositions may optionally comprise a catalyst to catalyze the reaction between the polymer and the curing agent (if present) or the self-crosslinking groups of the polymer (if present). Non-limiting examples of catalysts include latent acid catalysts, specific examples of which are identified in WO 2007/118024 at [0031] and include, but are not limited to, ammonium hexafluoroantimonate, quaternary salts of $SbF_6$ (e.g., NACURE® XC-7231), t-amine salts of $SbF_6$ (e.g., NACURE® XC-9223), Zn salts of triflic acid (e.g., NACURE® A202 and A218), quaternary salts of triflic acid (e.g., NACURE® XC-A230), and diethylamine salts of triflic acid (e.g., NACURE® A233), all commercially available from King Industries, and/or mixtures thereof. Latent acid catalysts may be formed by preparing a derivative of an acid catalyst such as para-toluenesulfonic acid (pTSA) or other sulfonic acids. For example, a group of blocked acid catalysts are amine salts of aromatic sulfonic acids, such as pyridinium para-toluenesulfonate. Such sulfonate salts are less active than the free acid in promoting crosslinking. During cure, some catalysts may be activated by heating.

According to the present invention, the aqueous resinous dispersions or curable film-forming compositions may comprise other optional ingredients, such as a pigment composition and, if desired, various additives such as fillers, plasticizers, anti-oxidants, biocides, auxiliary polymers or oligomers such as acrylics, polyesters, additional epoxy or phosphated epoxy resins (other than the phosphated epoxy resin described above), rheology modifiers, UV light absorbers and stabilizers, hindered amine light stabilizers, defoamers, fungicides, dispersing aids, flow control agents, surfactants, wetting agents, flatting agents to control gloss, or combinations thereof. Alternatively, the aqueous resinous dispersion or curable film-forming composition may be free of any of the optional ingredients, i.e., the optional ingredient is not present in the aqueous resinous dispersion or curable film-forming composition. The pigment content of the dispersion may be expressed as the pigment-to-resin weight ratio and may be within the range of 0.03:1 to 4.00:1, when pigment is present. The other additives mentioned above each may be present in the aqueous resinous dispersion or curable film-forming composition in amounts of 0.01% to 3% by weight, based on total weight of the resin solids of the aqueous resinous dispersion or curable film-forming composition.

According to the present invention, the total solids content of the aqueous resinous dispersion may be from 1% to 50% by weight, such as 5% to 40% by weight, such as 5% to 20% by weight, based on the total weight of the aqueous resinous dispersion. As used herein, "total solids" refers to the non-volatile content of the aqueous resinous dispersion, i.e., materials which will not volatilize when heated to 110° C. for 60 minutes.

A coating may be deposited from the aqueous resinous dispersion or curable film-forming composition onto a substrate. Accordingly, the present invention is also directed to a coating comprising the polymer comprising a pendant carbamate-functional moiety. The present invention is further directed to a substrate at least partially coated with a coating comprising the polymer comprising a pendant carbamate-functional moiety.

The present invention is also directed to methods of coating a substrate comprising applying the aqueous resinous dispersion or curable film-forming coating composition of the present invention to at least a portion of the substrate. The method may further comprise subjecting the substrate to curing conditions sufficient to at least partially cure the applied composition. The curing conditions may comprise any known in the art, such as, for example, air drying the composition under ambient conditions, heating the coated substrate, subjecting the coated substrate to UV radiation, and/or forced air curing. The method of coating may further comprise other optional steps, such as cleaning and/or degreasing the substrate, grit blasting the substrate surface, anodizing the substrate, pretreating the substrate prior to coating, such as by a metal phosphate pretreatment composition, a zirconium pretreatment composition, a trivalent chromium pretreatment composition, a solgel pretreatment composition, or a rare earth metal pretreatment composition, or other pretreatment compositions. The method may also optionally further comprise applying multiple coating layers, such as a primer, basecoat, and/or topcoat. The coating layers may be formed from the aqueous resinous dispersion or curable film-forming coating composition of the present invention. The additional coating layers can be prepared with any of the components described herein.

The aqueous resinous dispersions or curable film-forming coating compositions can be applied to a wide range of substrates known in the coatings industry. For example, the compositions of the present invention can be applied to automotive substrates (e.g. automotive vehicles including but not limited to cars, buses, trucks, trailers, etc.), industrial substrates, aerospace vehicle and aerospace vehicle components, marine substrates and components such as ships, vessels, and on-shore and off-shore installations, storage tanks, windmills, nuclear plants, packaging substrates, wood flooring and furniture, apparel, electronics, including housings and circuit boards, glass and transparencies, sports equipment, including golf balls, stadiums, buildings, bridges, and the like. These substrates can be, for example, metallic or non-metallic.

The metallic substrates comprise metal or metal alloy and may comprise cold rolled steel, hot rolled steel, steel coated with zinc metal, zinc compounds, or zinc alloys, such as electrogalvanized steel, hot-dipped galvanized steel, galvanealed steel, blasted/profiled steel, and steel plated with zinc alloy. As used herein, blasted or profiled steel refers to steel that has been subjected to abrasive blasting and which involves mechanical cleaning by continuously impacting the steel substrate with abrasive particles at high velocities using compressed air or by centrifugal impellers. The abrasives are typically recycled/reused materials and the process can efficiently removal mill scale and rust. The standard grades of cleanliness for abrasive blast cleaning is conducted in accordance with BS EN ISO 8501-1. Aluminum alloys of the 1XXX, 2XXX (such as the 2024 alloy), 3XXX, 4XXX, 5XXX, 6XXX, or 7XXX (such as the 7075 alloy) series as well as clad aluminum alloys and cast aluminum alloys of the A356 series also may be used as the substrate. Magnesium and magnesium alloys of the AZ31B, AZ91C, AM60B, or EV31A series also may be used as the substrate. The substrate used in the present invention may also comprise titanium and/or titanium alloys. Other suitable non-ferrous metals include copper and its alloys. Suitable metal substrates for use in the present invention include those that are often used in the assembly of vehicular bodies (e.g., without limitation, door, body panel, trunk deck lid, roof panel, hood, roof and/or stringers, rivets, landing gear components, and/or skins used on an aircraft), a vehicular frame, vehicular parts, motorcycles, wheels, industrial structures and components such as appliances, including washers, dryers, refrigerators, stoves, dishwashers, and the like, agricultural equipment, lawn and garden equipment, air conditioning units, heat pump units, lawn furniture, and other articles. The substrate may comprise a vehicle or a portion or part thereof. The term "vehicle" is used in its broadest sense and includes all types of aircraft, spacecraft, watercraft, and ground vehicles. For example, a vehicle may be an aerospace vehicle including aircraft such as airplanes including private aircraft, and small, medium, or large commercial passenger, freight, and military aircraft; helicopters, including private, commercial, and military helicopters; or rockets and other spacecraft. A vehicle can include a ground vehicle such as, for example, trailers, cars, trucks, buses, vans, construction vehicles, golf carts, motorcycles, bicycles, trains, and railroad cars. A vehicle can also include watercraft such as, for example, ships, boats, and hovercraft. The aqueous resinous dispersion or curable film-forming composition may be utilized to coat surfaces and parts thereof. A part may include multiple surfaces. A part may include a portion of a larger part, assembly, or apparatus. A portion of a part may be coated with the aqueous resinous dispersion or curable film-forming composition of the present invention or the entire part may be coated. The metal substrate may be in the shape of a cylinder, such as a pipe, including, for example, a cast iron pipe. The metal substrate also may be in the form of, for example, a sheet of metal or a fabricated part. The substrate may also comprise conductive or non-conductive substrates at least partially coated with a conductive coating. The conductive coating may comprise a conductive agent such as, for example, graphene, conductive carbon black, conductive polymers, or conductive additives.

Further, non-metallic substrates include polymeric, plastic, polyester, polyolefin, polyamide, cellulosic, polystyrene, polyacrylic, poly(ethylene naphthalate), polypropylene, polyethylene, nylon, EVOH, polylactic acid, other "green" polymeric substrates, poly(ethylene terephthalate) (PET), polycarbonate, polycarbonate acrylobutadiene styrene (PC/ABS), polyamide, composites, such as, for example, carbon fiber reinforced polymer composites, wood, veneer, wood composite, particle board, medium density fiberboard, cement, stone, glass, paper, cardboard, textiles, leather both synthetic and natural, and the like. It is appreciated that the compositions can be applied to various areas of any of the previously described substrates to form a continuous solid coating such as over the body and edges of a substrate.

It will also be understood that the substrate may be pretreated with a pretreatment solution. Non-limiting examples of a pretreatment solution include a zinc phosphate pretreatment solution such as, for example, those described in U.S. Pat. Nos. 4,793,867 and 5,588,989, a zirconium containing pretreatment solution such as, for example, those described in U.S. Pat. Nos. 7,749,368 and 8,673,091. Other non-limiting examples of a pretreatment solution include those comprising trivalent chromium, hexavalent chromium, lithium salts, permanganate, rare earth metals, such as yttrium, or lanthanides, such as cerium. Another non-limiting example of a suitable surface pretreatment solution is a solgel, such as those comprising alkoxysilanes, alkoxy-zirconates, and/or alkoxy-titanates.

The substrate may optionally be subjected to other treatments prior to coating. For example, the substrate may be cleaned, cleaned and deoxidized, anodized, acid pickled, plasma treated, laser treated, or ion vapor deposition (IVD) treated. These optional treatments may be used on their own or in combination with a pretreatment solution. The substrate may be new (i.e., newly constructed or fabricated) or it may be refurbished, such as, for example, in the case of refinishing or repairing a component of an automobile or aircraft.

Alternatively, the substrate may be a non-pretreated substrate, such as a bare substrate, that is not pretreated by a pretreatment solution.

As mentioned above, the substrate coated by the aqueous resinous dispersion or curable film-forming composition of the present invention may comprise a vehicle. For example, the aqueous resinous dispersion or curable film-forming composition of the present invention may be utilized in coating a F/A-18 jet or related aircraft such as the F/A-18E Super Hornet and F/A-18F (produced by McDonnell Douglas/Boeing and Northrop); in coating the Boeing 787 Dreamliner, 737, 747, 717 passenger jet aircraft, and related aircraft (produced by Boeing Commercial Airplanes); in coating the V-22 Osprey; VH-92, S-92, and related aircraft (produced by NAVAIR and Sikorsky); in coating the G650, G600, G550, G500, G450, and related aircraft (produced by Gulfstream); and in coating the A350, A320, A330, and related aircraft (produced by Airbus). The aqueous resinous dispersion or curable film-forming composition may be used as a coating for use in any suitable commercial, military, or general aviation aircraft such as, for example, those produced by Bombardier Inc. and/or Bombardier Aerospace such as the Canadair Regional Jet (CRJ) and related aircraft; produced by Lockheed Martin such as the F-22 Raptor, the F-35 Lightning, and related aircraft; produced by Northrop Grumman such as the B-2 Spirit and related aircraft; produced by Pilatus Aircraft Ltd.; produced by Eclipse Aviation Corporation; or produced by Eclipse Aerospace (Kestrel Aircraft).

The aqueous resinous dispersion or curable film-forming composition may also be used to coat surfaces of vehicles. Non-limiting examples thereof include fuel tank surfaces and other surfaces exposed to or potentially exposed to aerospace solvents, aerospace hydraulic fluids, and aerospace fuels.

The aqueous resinous dispersion or curable film-forming composition can be applied to a substrate to form a monocoat. As used herein, a "monocoat" refers to a single layer coating system that is free of additional coating layers. Thus, the coating composition of the present invention can be applied directly to a substrate and cured to form a single layer coating, i.e. a monocoat.

Alternatively, the aqueous resinous dispersion or curable film-forming composition may be applied to a substrate as part of a multi-layer coating system. It is appreciated that the multi-layer coating may comprise multiple coating layers such as three or more, or four or more, or five or more, coating layers. For example, the multiple coating layers may include a primer, basecoat(s) and/or topcoat(s) layers, and the aqueous resinous dispersion or curable film-forming composition may comprise any one or all of such layers. As used herein, a "primer" refers to a coating composition from which an undercoating may be deposited onto a substrate in order to prepare the surface for application of a protective or decorative coating system. A "basecoat" refers to a coating composition from which a coating is deposited onto a primer and/or directly onto a substrate, optionally including components (such as pigments) that impact the color and/or provide other visual impact, and which may be overcoated with a protective and decorative topcoat. For example, the aqueous resinous dispersion or curable film-forming composition may be used as a colored basecoat or a clearcoat for an automotive or aerospace vehicle.

The aqueous resinous dispersions of the present invention may comprise and be in the form of an electrodepositable coating composition. As used herein, the term "electrodepositable coating composition" refers to a composition that is capable of being deposited onto an electrically conductive substrate under the influence of an applied electrical potential.

A coating may be electrophoretically deposited onto a substrate from the electrodepositable coating composition. The electrodeposited coating layer may be applied by methods known in the art. After the coating is electrophoretically deposited onto the substrate, the coating may be subjected to curing conditions that at least partially cure the deposited coating. For example, the coated substrate may be heated to a temperature and for a time sufficient to at least partially cure the electrodeposited coating on the substrate. One or more additional coating layers may be applied onto the electrodeposited coating layer. The additional coating layer may be applied onto the electrodeposited coating layer prior to or after curing the electrodeposited coating layer, and the additional coating layer may be subjected to curing conditions to at least partially cure such coating layer alone or simultaneously with the electrodeposited coating layer. Non-limiting examples of external energy sources that may provide suitable curing conditions for curing the electrodeposited layer and/or additional coating layers include thermal energy and radiation such as ultraviolet, infrared or microwave.

Substrates suitable to have a coating electrophoretically deposited thereon include conductive substrates, such as metal substrates, metal alloy substrates, and/or substrates that have been metallized (e.g., nickel-plated plastic), as well as substrates comprising non-metal conductive materials including composite materials such as, for example, materials comprising carbon fibers or conductive carbon. Examples of these substrates are provided above.

Alternatively, the coating may be deposited from the aqueous resinous dispersion or curable film-forming composition by any other method known in the art, such as, for example, dip, roll, brush, spray, electrostatic spray, or by the use of a fluidized bed.

The coating deposited from the aqueous resinous dispersions or curable film-forming compositions comprising the polymer of the present invention may be hydrolytically stable, as determined by the Hydrolytic Stability Test Method. As used herein, the "Hydrolytic Stability Test Method" refers to immersing a baked panel in deionized water at a temperature of 90° C. for 24 hours. The panel is then removed and baked in an oven set to 150° F. for 60 minutes to dehydrate the coating film. The panel is then retested for cure according to the Double Acetone Rub Test Method and compared to the cure of the panel by the Double Acetone Rub Test Method prior to the water soak. Whether a coating is considered to be hydrolytically stable is demonstrated by the ability of the coating to retain acetone resistance after being subjected to the water soak compared to the acetone resistance of the coating without the water soak. Specifically, the number of double acetone rubs that the coating survived following the water soak is compared to the number of double acetone rubs the coating survived without exposure to the water soak. A coating is considered to be "hydrolytically stable" if the coating survived a number of double acetone rubs following exposure to the water soak without reaching the underlying substrate equal to at least 60% of the double acetone rubs that the coating was able to survive without exposure to the water soak, with the caveat that if the cured coating survived 100 or more double acetone rubs without exposure to the water soak, then the cured coating was considered to be hydrolytically stable if the coating survived at least 60 double acetone rubs without reaching the substrate. For example, a coating that survived 50 double acetone rubs without exposure to the water soak was considered to be hydrolytically stable if it survived at least 30 double acetone rubs following exposure to the water soak. Although reference is made to the coating prior to exposure to the water soak and after exposure to the water soak, it should be understood that two different coated panels are used with each panel having been coated by the same composition by the same technique and cured under the same conditions (i.e., same oven, oven temperature and baking time).

The hydrolytic stability of the cured coatings derived from the aqueous resinous dispersion or curable film-forming composition was a surprising discovery. Without intending to be bound by any theory, it is believed that the carbamate functional group of the polymer forms bonds with curing agents that are not substantially susceptible to hydrolytic attack.

As used herein, the "Double Acetone Rub Test Method" refers to rubbing the baked panels with an acetone soaked WYPALL X80 disposable paper wipe manufactured by Kimberly-Clark. The number of double acetone rub(s) (one rub forward and rub backward constitutes a double rub) are counted until the coating is removed and the metal substrate is exposed, or until a predetermined number of rubs is reached without exposing the underlying substrate surface. A coating may be considered to be cured if it survives at least 25 double acetone rubs without reaching the substrate; such as at least 50 double acetone rubs without reaching the substrate; such as at least 75 double acetone rubs without reaching the substrate; such as at least 100 double acetone rubs without reaching the substrate.

As used herein, the "resin solids" include the polymer, the curing agent, the carbamate-functional oligomer (if present), the phosphated epoxy resin (if present), and any additional water-dispersible non-pigmented component(s) present in the composition.

As used herein, the term "alkyl" refers to a substituted or unsubstituted hydrocarbon chain that may be linear or branched and may comprise one or more hydrocarbon rings that are not aromatic. As used herein, "aryl" refers to a substituted or unsubstituted hydrocarbon having a delocalized conjugated π-system with alternating double and single bonds between carbon atoms forming one or more coplanar hydrocarbon rings.

For purposes of the detailed description, it is to be understood that the invention may assume various alternative variations and step sequences, except where expressly specified to the contrary. Moreover, other than in any operating examples, or where otherwise indicated, all numbers such as those expressing values, amounts, percentages, ranges, subranges and fractions may be read as if prefaced by the word "about," even if the term does not expressly appear. Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where a closed or open-ended numerical range is described herein, all numbers, values, amounts, percentages, subranges and fractions within or encompassed by the numerical range are to be considered as being specifically included in and belonging to the original disclosure of this application as if these numbers, values, amounts, percentages, subranges and fractions had been explicitly written out in their entirety.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

As used herein, unless indicated otherwise, a plural term can encompass its singular counterpart and vice versa, unless indicated otherwise. For example, although reference is made herein to "an" isocyanato functional unsaturated monomer, "a" hydroxyl functional, carbamate functional monomer, and "a" curing agent, a combination (i.e., a plurality) of these components can be used. In addition, in this application, the use of "or" means "and/or" unless specifically stated otherwise, even though "and/or" may be explicitly used in certain instances.

As used herein, "including," "containing" and like terms are understood in the context of this application to be synonymous with "comprising" and are therefore open-ended and do not exclude the presence of additional undescribed or unrecited elements, materials, ingredients or method steps. As used herein, "consisting of" is understood in the context of this application to exclude the presence of any unspecified element, ingredient or method step. As used herein, "consisting essentially of" is understood in the context of this application to include the specified elements, materials, ingredients or method steps "and those that do not materially affect the basic and novel characteristic(s)" of what is being described.

As used herein, the terms "on," "onto," "applied on," "applied onto," "formed on," "deposited on," "deposited onto," mean formed, overlaid, deposited, or provided on but not necessarily in contact with the surface. For example, an electrodepositable coating composition "deposited onto" a substrate does not preclude the presence of one or more other intervening coating layers of the same or different composition located between the electrodepositable coating composition and the substrate.

Whereas specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

Aspects

In view of the foregoing, the present invention relates inter alia, without being limited thereto, to the following aspects:

Aspect 1. A compound of formula I,

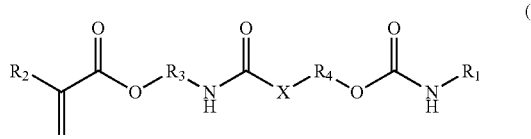

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_4$ comprises, consists essentially of, or consists of a divalent organic group; and X comprises, consists essentially of, or consists of oxygen, NH, or $N(R_5)$, wherein $R_5$ comprises, consists essentially of, or consists of a monovalent organic group.

Aspect 2. The compound of Aspect 1, wherein $R_3$ comprises, consists essentially of, or consists of the structure:

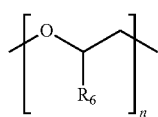

wherein n is a positive integer from 1 to 100.

Aspect 3. The compound of Aspect 2, wherein n is 1.
Aspect 4. The compound of any one of the preceding Aspects, wherein $R_4$ comprises, consists essentially of, or consists of the structure:

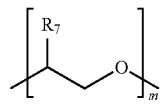

wherein m is a positive integer from 1 to 100.
Aspect 5. The compound of Aspect 4, wherein m is 1.
Aspect 6. The compound of any one of the preceding Aspects, wherein X comprises, consists essentially of, or consists of oxygen.
Aspect 7. The compound of any one of Aspects 1 to 5, wherein X comprises, consists essentially of, or consists of NH.
Aspect 8. The compound of any one of Aspects 1 to 5, wherein X comprises, consists essentially of, or consists of $N(R_5)$.
Aspect 9. The compound of any one of the preceding Aspects, wherein the compound comprises the structure:

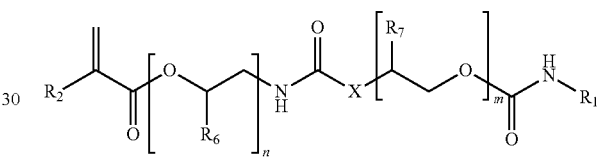

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; m is a positive integer from 1 to 100; and n is a positive integer from 1 to 100.

Aspect 10. The compound of any one of Aspects 1 to 8, wherein the compound comprises the structure:

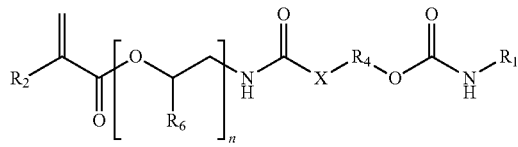

wherein $R_1$ comprises, consists essentially of, or consists of hydrogen, an alkyl group, or an aryl group; $R_2$ comprises, consists essentially of, or consists of hydrogen or a methyl group; $R_4$ comprises, consists essentially of, or consists of a divalent organic group; $R_6$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and n is a positive integer from 1 to 100.

Aspect 11. The compound any one of Aspects 1 to 8, wherein the compound comprises the structure:

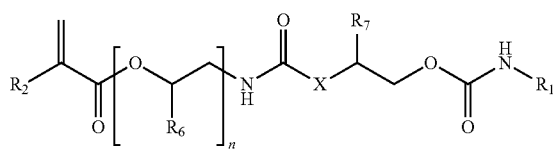

wherein $R_1$ comprises, consists essentially of, or consists of hydrogen, an alkyl group, or an aryl group; $R_2$ comprises, consists essentially of, or consists of hydrogen or a methyl group; $R_6$ comprises, consists essentially of, or consists of hydrogen or a methyl group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and n is a positive integer from 1 to 100.

Aspect 12. The compound of any one Aspects 1 to 8, wherein the compound comprises the structure:

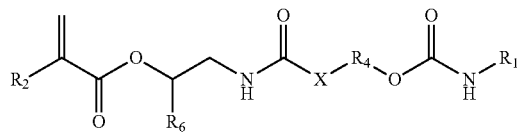

wherein $R_1$ comprises, consists essentially of, or consists of hydrogen, an alkyl group, or an aryl group; $R_2$ comprises, consists essentially of, or consists of hydrogen or a methyl group; $R_4$ comprises, consists essentially of, or consists of a divalent organic group; $R_6$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

Aspect 13. The compound of any one of Aspects 1 to 8, wherein the compound comprises the structure:

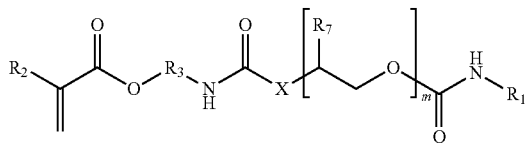

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_7$ comprises, consists essentially of, or consists of hydrogen or a methyl group; X comprises, consists essentially of, or consists of oxygen, NH, or $N(R_5)$ wherein $R_5$ comprises, consists essentially of, or consists of a monovalent organic group; and m is a positive integer from 1 to 100.

Aspect 14. The compound of any one of Aspects 1 to 8, wherein the compound comprises the structure:

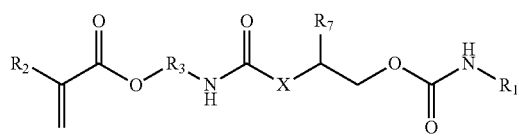

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_7$ comprises, consists essentially of, or consists of hydrogen or a methyl group; and X comprises, consists essentially of, or consists of oxygen, NH, or $N(R_5)$ wherein $R_5$ comprises, consists essentially of, or consists of a monovalent organic group.

Aspect 15. The compound of Aspect 6, wherein the compound comprises the structure:—

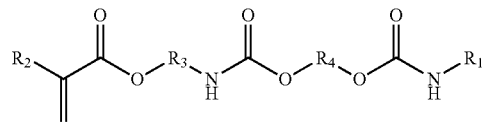

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and $R_4$ comprises, consists essentially of, or consists of a divalent organic group.

Aspect 16. The compound of Aspect 8, wherein the compound comprises the structure:

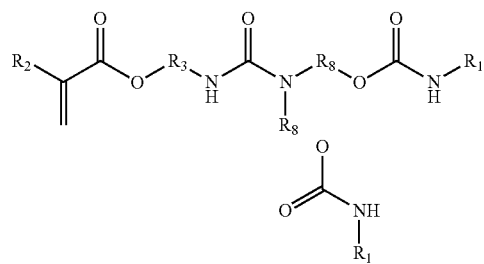

wherein each $R_1$ independently comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; each $R_7$ independently comprises, consists essentially of, or consists of hydrogen or a methyl group; and each $R_8$ independently comprises, consists essentially of, or consists of a divalent organic group.

Aspect 17. The compound of Aspect 8, wherein the compound comprises the structure:

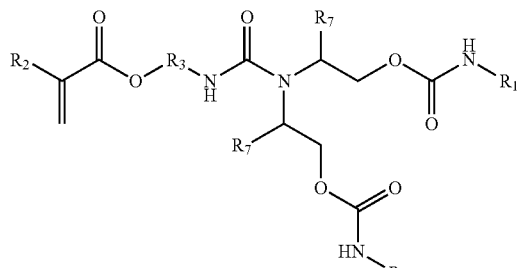

wherein each $R_1$ independently comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and each $R_7$ independently comprises, consists essentially of, or consists of hydrogen or a methyl group.

Aspect 18. The compound of Aspect 8, wherein the compound comprises the structure:

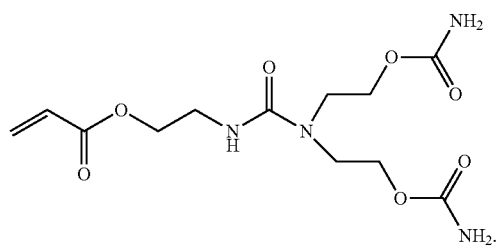 [SMILES: C=CC(=O)OCCNC(=O)N(CCOC(N)=O)CCOC(N)=O]

Aspect 19. The compound of Aspect 6, wherein the compound comprises the structure:

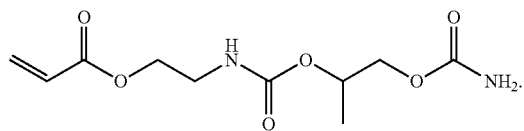 [SMILES: C=CC(=O)OCCNC(=O)OC(C)COC(N)=O]

Aspect 20. A polymer comprising a pendant carbamate-functional moiety comprising the structure:

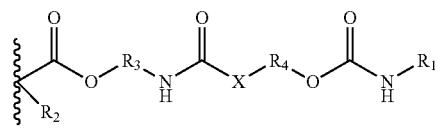

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; $R_4$ comprises, consists essentially of, or consists of a divalent organic group; and X comprises, consists essentially of, or consists of oxygen, NH, or $N(R_5)$ wherein $R_5$ comprises, consists essentially of, or consists of a monovalent organic group.

Aspect 21. The polymer of Aspect 20, wherein the polymer comprises the residue of the compound of any one of the Aspects 1 to 19.

Aspect 22. A curable film-forming composition comprising the polymer of Aspect 20 or Aspect 21.

Aspect 23. An aqueous dispersion comprising the polymer of Aspect 20 or Aspect 21.

Aspect 24. A coating comprising the polymer of Aspect 20 or Aspect 21.

Aspect 25. A method of preparing the compound of Aspect 6, the method comprising the step of reacting an isocyanato functional unsaturated monomer of formula II with a hydroxyl functional, carbamate functional monomer according to formula III,

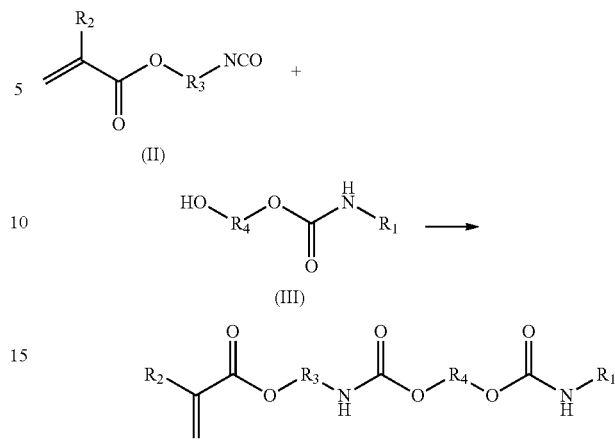

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; and $R_4$ comprises, consists essentially of, or consists of a divalent organic group.

Aspect 26. A method of preparing the compound of Aspect 8, the method comprising the steps of (1) reacting an isocyanato functional unsaturated compound of formula II with a dihydroxy alkyl amine compound of formula IV to form a reaction product,

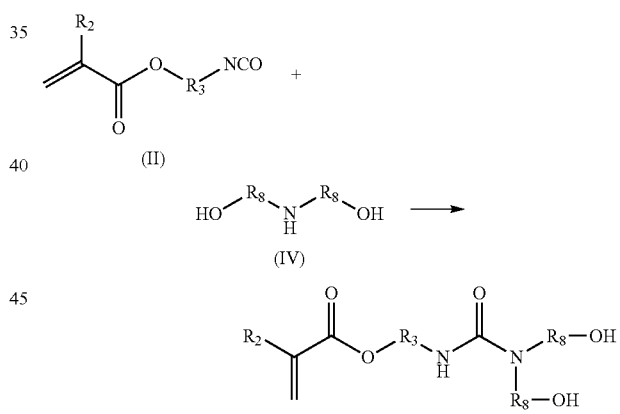

and (2) further reacting the reaction product with a carbamate ester according to formula V,

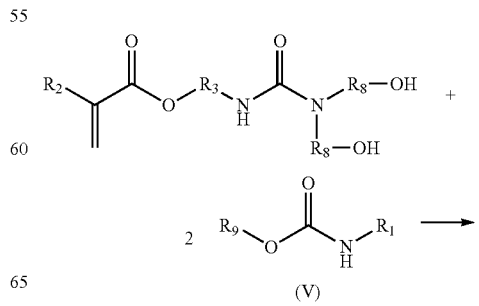

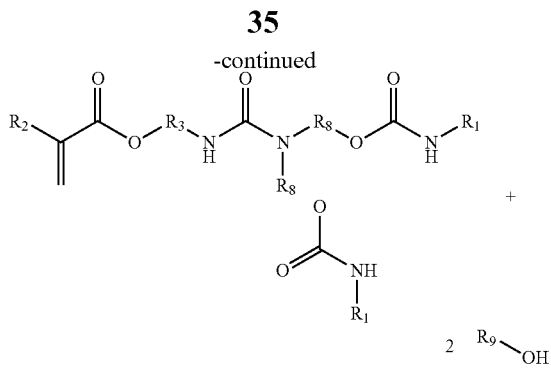

wherein $R_1$ comprises, consists essentially of, or consists of hydrogen, an alkyl group, or an aryl group; $R_2$ comprises, consists essentially of, or consists of hydrogen or a methyl group; $R_3$ comprises, consists essentially of, or consists of a divalent organic group; each $R_8$ independently comprises, consists essentially of, or consists of a divalent organic group; and $R_9$ comprises, consists essentially of, or consists of a monovalent organic group.

Illustrating the invention are the following examples, which, however, are not to be considered as limiting the invention to their details. Unless otherwise indicated, all parts and percentages in the following examples, as well as throughout the specification, are by weight.

EXAMPLES

Example 1: Preparation of a Carbamate Functional, Ethylenically Unsaturated Monomer A carbamate functional, ethylenically unsaturated monomer was prepared as follows:

TABLE 1

| # | Material | Amount (g) |
|---|---|---|
| 1 | Carbalink HPC (95%)[1] | 255.8 |
| 2 | 2,6-Di-tert-butyl-4-methylphenol | 0.5 |
| 3 | Dibutyltindilaurate | 1.0 |
| 4 | Karenz AOI[2] | 282.2 |

[1]Hydroxypropyl carbamate commercially available from Huntsman Corp.
[2]2-Isocyanatoethyl acrylate. Available commercially from Karenz.

Charges 1-3 were added to a flask set up for total reflux with stirring under ambient air conditions. The mixture was heated to a temperature of 60° C. Charge 4 was added dropwise through an addition funnel while the resulting exotherm was maintained under 70° C. The mixture was held for 5 hours at 60° C. After holding, the mixture revealed no residual isocyanate peak by IR (2200-2300 cm$^{-1}$). The mixture was cooled to 30° C. and poured out. Final solids were 96.4%.

A reaction scheme for production of this monomer is as follows:

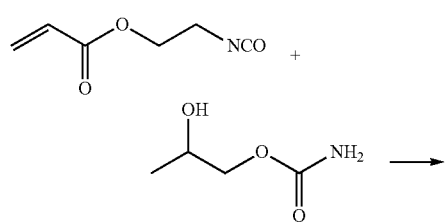

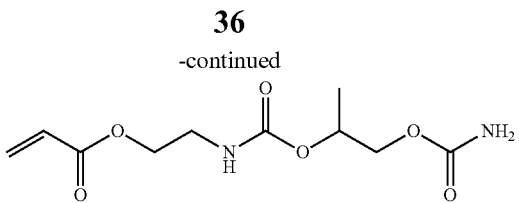

Example 2: Preparation of a Polymer Including Phosphorous Acid and Carbamate Functional Groups and an Aqueous Dispersion of Said Polymer and a Curing Agent A polymer including phosphorous acid and carbamate functional groups was prepared as follows:

TABLE 2

| # | Material | Amount (g) |
|---|---|---|
| 1 | Butanol | 77.5 |
| 2 | Methacrylic acid | 35.4 |
| 3 | Styrene | 60.2 |
| 4 | Butyl acrylate | 94.5 |
| 5 | Carbamate Functional, Ethylenically Unsaturated Monomer Mixture from Example 1 | 245.8 |
| 6 | t-dodecylmercaptan | 14.5 |
| 7 | Butanol | 37.4 |
| 8 | t-butylperbenzoate | 5.4 |
| 9 | Butanol | 42.8 |
| 10 | Sipomer PAM-200[1] | 22.4 |
| 11 | Diisopropanolamine | 13.0 |
| 12 | Butanol | 8.4 |
| 13 | t-butylperbenzoate | 1.2 |
| 14 | Deionized water | 32.6 |
| 15 | Diisopropanolamine | 40.9 |
| 16 | Deionized water | 3.5 |
| 17 | CYMEL 1130[2] | 192.5 |
| 18 | Deionized water | 468.9 |
| 19 | Deionized water | 267.8 |
| 20 | Deionized water | 446.4 |

[1]Sipomer PAM-200 is a methacrylate monomer supplied by Rhodia Solvay Group containing a phosphonic acid functional group.
[2]A methylated/n-butylated melamine-formaldehyde curing agent available from Allnex.

Charge 1 was added to a flask set up for total reflux with stirring under nitrogen and heated to 115° C. Charges 2-11 (with charges 9-11 premixed) were slowly added via addition funnel over 180 minutes and the reaction mixture was then held at 115° C. for an additional 30 minutes. Charges 12-13 were then added dropwise in 2 portions over separate 60-minute intervals. The reaction mixture was then held for an additional 60 minutes at 115° C. Then 124 g of butanol were distilled off from the reaction mixture under vacuum. The reaction mixture was then cooled to 105° C., charge 14 was added slowly, and then the reaction mixture was cooled to 95° C. Charges 15-16 were then added and the reaction mixture held for 30 minutes. Charge 17 was added and the reaction mixture was held for an additional 30 minutes. The resulting mixture was then reverse thinned into charge 18, which was at ambient temperature, and held for 30 minutes. Charge 19 was then added and the reaction mixture was held for 30 minutes. Finally, charge 20 was added and the reaction mixture was held for 30 minutes. Final solids were 29.9%. Final molecular weight as determined by GPC ($M_z$) was 191,872 g/mol.

Example 3: Preparation of a Pigmented Aqueous Resinous Dispersion of the Aqueous Resinous Dispersion of Example 2 and Electrodeposition Thereof A pigmented aqueous resinous dispersion of the dispersion of the addition polymer including phosphorous acid and carbamate functionality and a curing agent from Example 2 was prepared as follows:

TABLE 3

| # | Material | Amount (g) |
|---|----------|------------|
| 1 | Dispersion of Addition Polymer of Example 2 | 1469.9 |
| 2 | ACPP2220 | 239.0 |
| 3 | Deionized water | 1091.28 |

[1] Commercially available electrocoat pigment paste available through PPG Industries, Inc.

Charge 1 was added to a 1-gallon plastic bucket and agitation was started. Charge 2 was added slowly over 5 minutes. Finally, charge 3 was added over 5 minutes and the resulting mixture stirred for an additional 15 minutes.

After ultrafiltration, the paint was electrodeposited (applied at a voltage of 190V for 90 s duration with a bath temperature of 80° F.) onto a 2024 T3 aluminum substrate and baked in an oven set to a temperature of 250° F. for 60 minutes. Cure testing by the Double Acetone Rub Test Method revealed that the film withstood 86 double acetone rubs (DAR) before reaching the metal. The film also passed crosshatch adhesion testing performed according to ISO 2409.

The film was then immersed in water at a temperature of 90° C. for 24 hours. It was then removed and baked in an oven set to 150° F. for 60 minutes to dehydrate the film. Upon retesting for cure using the Double Acetone Rub Test Method, the film withstood 79 DAR before reaching the metal.

Comparative Example 4: Preparation of Comparative Addition Polymer Having Carboxylic Acid and Hydroxyl Functional Groups and an Aqueous Dispersion of the Comparative Addition Polymer and a Curing Agent A comparative addition polymer having carboxylic acid and hydroxyl functional groups, without phosphorous acid or carbamate functional groups, and aqueous dispersion of the same with a curing agent was prepared as follows:

TABLE 4

| # | Material | Amount (g) |
|---|----------|------------|
| 1 | Dowanol PM | 217.4 |
| 2 | Butyl CELLOSOLVE | 133.7 |
| 3 | Methyl methacrylate | 552.8 |
| 4 | 2-Ethylhexyl acrylate | 106.4 |
| 5 | Hydroxyethyl acrylate | 138.2 |
| 6 | Butyl acrylate | 53.1 |
| 7 | Styrene | 127.5 |
| 8 | Acrylic acid | 85.1 |
| 9 | tert.Butylperoxy-2-ethylhexanoate | 12.8 |
| 10 | Butyl CELLOSOLVE | 28.8 |
| 11 | Isopropanol | 31.1 |
| 12 | tert.Butylperoxy-2-ethylhexanoate | 3.8 |
| 13 | Isopropanol | 259.7 |
| 14 | CYMEL 1130 | 739.4 |
| 15 | CoatOSil 7602[1] | 9.2 |
| 16 | Butanol | 101.7 |
| 17 | Dimethylethanol amine | 28.8 |
| 18 | Triethylamine | 33.0 |
| 19 | Deionized water | 65.7 |
| 20 | Deionized water | 654.3 |
| 21 | Deionized water | 1042.7 |

[1] CoatOSil 7602 is a silicone copolymer available from Momentive

Charges 1 and 2 were added to a flask set up for total reflux with stirring under nitrogen and heated to 100° C. Charges 3-11 were slowly added via addition funnel over 180 minutes and the reaction mixture was then held at 100° C. for an additional 30 minutes. Charges 12-13 were then added dropwise in 3 portions over separate 60-minute intervals. The reaction mixture was then held at 100° C. for 60 minutes. Charges 14-16 were then added and the reaction mixture held at 100° C. for 15 minutes. The product was cooled to 90° C. and charges 17-19 were added and the reaction mixture held for an additional 15 minutes. The resulting mixture was then reverse thinned into charge 20, which was at ambient temperature, and the resulting mixture was held for 30 minutes. Finally, charge 21 was added and the mixture was held for an additional 30 minutes. Final solids were 29.8%. Final molecular weight as determined by GPC ($M_z$) was 120,311 g/mol.

Comparative Example 5: Preparation of a Pigmented Comparative Aqueous Resinous Dispersion of Example 4 and Electrodeposition Thereof A comparative pigmented aqueous resinous dispersion of the comparative addition polymer and curing agent dispersion of Example 4 was prepared as follows:

TABLE 5

| # | Material | Amount (g) |
|---|----------|------------|
| 1 | Dispersion of Addition Polymer of Example 4 | 1735.2 |
| 2 | ACPP2220[1] | 271.4 |
| 3 | Deionized water | 1193.5 |

[1] Commercially available electrocoat pigment paste available through PPG Industries, Inc.

Charge 1 was added to a 1-gallon plastic bucket and agitation was started. Charge 2 was added slowly over 5 minutes. Finally, charge 3 was added over 5 minutes and the resulting mixture stirred for an additional 15 minutes.

After ultrafiltration, the paint was electrodeposited (applied at a voltage of 280V for 90 s duration with a bath temperature of 80° F./) onto a 2024 T3 aluminum substrate and baked in an oven set to a temperature of 250° F. for 60 minutes. Cure testing by the Double Acetone Rub Test Method revealed that the film was not fully cured (20 DAR to metal).

After initial cure testing, 1.5% (on paint solids) Nacure 1051 (acid catalyst based on dinonylnapthalene sulfonic acid available from King Industries) was added as a free species to the paint bath and cure testing was performed again. The film now passed 100 DAR after a 60-minute bake at 250° F. However, the film was left with no adhesion to the substrate, as it did not pass crosshatch adhesion testing performed according to ISO 2409.

Comparative Example 6: Preparation of a Comparative Addition Polymer Having Phosphorous Acid and Hydroxyl Functional Groups and Aqueous Resinous Dispersion of the Comparative Addition Polymer and a Curing Agent A comparative addition polymer having phosphorous acid and hydroxyl functional groups, without carbamate functional groups, and an aqueous dispersion of the same with a curing agent was prepared as follows:

TABLE 6

| # | Material | Amount (g) |
|---|---|---|
| 1 | Butanol | 77.5 |
| 2 | Methacrylic acid | 35.4 |
| 3 | Styrene | 71.4 |
| 4 | Butyl acrylate | 210.0 |
| 5 | Hydroxyethyl acrylate | 109.9 |
| 6 | t-dodecylmercaptan | 14.5 |
| 7 | Butanol | 37.4 |
| 8 | t-butylperbenzoate | 5.4 |
| 9 | Butanol | 42.8 |
| 10 | Sipomer PAM-200[1] | 22.4 |
| 11 | Diisopropanolamine | 13.0 |
| 12 | Butanol | 8.4 |
| 13 | t-butylperbenzoate | 1.2 |
| 14 | Deionized water | 32.6 |
| 15 | Diisopropanolamine | 40.9 |
| 16 | Deionized water | 3.5 |
| 17 | CYMEL 1130 | 192.5 |
| 18 | Deionized water | 473.7 |
| 19 | Deionized water | 267.3 |
| 20 | Deionized water | 445.5 |

[1]Sipomer PAM-200 is a methacrylate monomer supplied by Rhodia Solvay Group containing a phosphonic acid functional group Charge 1 was added to a flask set up for total reflux with stirring under nitrogen and heated to 115° C. Charges 2-11 (with charges 9-11 premixed) were slowly added via addition funnel over 180 minutes and the resulting mixture was then held at 115° C. for an additional 30 minutes. Charges 12-13 were then added dropwise in 2 portions over separate 60-minute intervals. The reaction mixture was then held for an additional 60 minutes at 115° C. Then 124 g of butanol were distilled off from the reaction mixture under vacuum. The reaction mixture was then cooled to 105° C., charge 14 was added slowly, and then the reaction mixture was cooled to 95° C. Charges 15-16 were then added and the reaction mixture held for 30 minutes. Charge 17 was added and held for an additional 30 minutes. The resulting mixture was then reverse thinned into charge 18, which was at ambient temperature, and the mixture was held for 30 minutes. Charge 19 was then added and the mixture was held for 30 minutes. Finally, charge 20 was added and held for 30 minutes. Final solids were 28.7%. Final molecular weight as determined by GPC ($M_z$) was 95,804 g/mol.

Comparative Example 7: Preparation of a Comparative Pigmented Aqueous Resinous Dispersion of the Aqueous Resinous Dispersion of Example 6 and Electrodeposition Thereof A comparative pigmented aqueous resinous dispersion of the comparative addition polymer and curing agent dispersion of Example 6 was prepared as follows:

TABLE 7

| # | Material | Amount (g) |
|---|---|---|
| 1 | Dispersion of Addition Polymer of Example 6 | 1530.7 |
| 2 | ACPP2220[1] | 239.0 |
| 3 | Deionized water | 1030.3 |

[1]Commercially available electrocoat pigment paste available through PPG Industries, Inc.

Charge 1 was added to a 1-gallon plastic bucket and agitation was started. Charge 2 was added slowly over 5 minutes. Finally, charge 3 was added over 5 minutes and the resulting mixture stirred for an additional 15 minutes.

After ultrafiltration, the paint was electrodeposited (applied voltage of 150V for 90 s duration with a bath temperature of 75° F.) onto a 2024 T3 aluminum substrate and baked in an oven set to a temperature of 250° F. for 60 minutes. Cure testing by the Double Acetone Rub Test Method revealed that the film was fully cured (100 DAR). The film also passed crosshatch adhesion testing performed according to ISO 2409.

The film was then immersed in water at a temperature of 90° C. for 24 hours. It was then removed and baked in an oven set to 150° F. for 60 minutes to dehydrate the film. Upon retesting for cure using the Double Acetone Rub Test Method, the film failed to metal after only 10 rubs.

Example 8: Preparation of a Polymer Including Sulfonic Acid and Carbamate Functional Groups and an Aqueous Dispersion of Said Polymer and a Curing Agent A polymer including sulfonic acid and carbamate functional groups was prepared as follows:

TABLE 8

| Charge | Material | Amount (g) |
|---|---|---|
| 1 | Butanol | 55.4 |
| 2 | Methacrylic acid | 25.3 |
| 3 | Styrene | 50.0 |
| 4 | Butyl acrylate | 110.8 |
| 5 | Carbamate Functional, Ethylenically Unsaturated Monomer Mixture from Example 1 | 174.5 |
| 6 | t-dodecylmercaptan | 10.4 |
| 7 | Butanol | 26.7 |
| 8 | t-butylperbenzoate | 3.8 |
| 9 | Butanol | 30.6 |
| 10 | 2-Acrylamide-2-methylpropane sulfonic acid (AMPS) | 6.5 |
| 11 | Diisopropanolamine | 4.4 |
| 12 | Butanol | 6.0 |
| 13 | t-butylperbenzoate | 0.9 |
| 14 | Deionized water | 23.3 |
| 15 | Diisopropanolamine | 30.4 |
| 16 | Deionized water | 2.5 |
| 17 | Cymel 1130[1] | 127.5 |
| 18 | Deionized water | 365.4 |

[1]A methylated/n-butylated melamine-formaldehyde curing agent available from Allnex.

Charge 1 was added to a flask set up for total reflux with stirring under nitrogen and heated to 115° C. Charges 2-11 (with charges 9-11 premixed) were slowly added via addition funnel over 180 minutes and the reaction mixture was then held at 115° C. for an additional 30 minutes. Charges 12-13 were then added dropwise in 2 portions over separate 60-minute intervals. The reaction mixture was then held for an additional 60 minutes at 115° C. Then 113 g of butanol were distilled off from the reaction mixture under vacuum. The reaction mixture was then cooled to 105° C., charge 14 was added slowly, and then the reaction mixture was cooled to 95° C. Charges 15-16 were then added and the reaction mixture held for 30 minutes. Charge 17 was added and the reaction mixture was held for an additional 30 minutes. The resulting mixture was then reverse thinned into charge 18, which was at ambient temperature, and held for 30 minutes. Charge 19 was then added and the reaction mixture was held for 30 minutes. Finally, charge 20 was added and the reaction mixture was held for 30 minutes. Final solids were 30.0%. Final molecular weight as determined by GPC ($M_z$) was 222,587 g/mol.

Example 9: Preparation of a Pigmented Aqueous Resinous Dispersion of the Aqueous Resinous Dispersion of Example 8 and Electrodeposition Thereof A pigmented aqueous resinous dispersion of the dispersion of the addition polymer including sulfonic acid and carbamate functional groups and a curing agent from Example 8 was prepared as follows:

TABLE 9

| Charge | Material | Amount (g) |
|---|---|---|
| 1 | Dispersion of Addition Polymer of Example 8 | 1319.0 |
| 2 | ACPP2220[1] | 215.6 |
| 3 | Deionized water | 991.6 |

[1]Commercially available electrocoat pigment paste available through PPG Industries, Inc.

Charge 1 was added to a 1-gallon plastic bucket and agitation was started. Charge 2 was added slowly over 5 minutes. Finally, charge 3 was added over 5 minutes and the resulting mixture stirred for an additional 15 minutes.

After ultrafiltration, the paint was electrodeposited (applied at a voltage of 160V for 90 s duration with a bath temperature of 75° F.) onto a 2024 T3 aluminum substrate and baked in an oven set to a temperature of 250° F. for 60 minutes. Cure testing by the Double Acetone Rub Test Method revealed that the film was fully cured (100 DAR). The film also passed crosshatch adhesion testing performed according to ISO 2409.

The film was then immersed in water at a temperature of 90° C. for 24 hours. It was then removed and baked in an oven set to 150° F. for 60 minutes to dehydrate the film. Upon retesting for cure Double Acetone Rub Test Method, the film was still fully cured (100 DAR).

Comparative Example 10: Preparation of Comparative Addition Polymer Having Carboxylic Acid and Hydroxyl Functional Groups and an Aqueous Dispersion of the Comparative Addition Polymer and Curing Agent A comparative addition polymer having carboxylic acid and hydroxyl functional groups, without sulfonic acid or carbamate functional groups, and aqueous dispersion of the same with a curing agent was prepared as follows:

TABLE 10

| Charge | Material | Amount (g) |
|---|---|---|
| 1 | DOWANOL PM[1] | 217.4 |
| 2 | Butyl CELLOSOLVE[2] | 133.7 |
| 3 | Methyl methacrylate | 552.8 |
| 4 | 2-Ethylhexyl acrylate | 106.4 |
| 5 | Hydroxyethyl acrylate | 138.2 |
| 6 | Butyl acrylate | 53.1 |
| 7 | Styrene | 127.5 |
| 8 | Acrylic acid | 85.1 |
| 9 | tert.Butylperoxy-2-ethylhexanoale | 12.8 |
| 10 | Butyl CELLOSOLVE | 28.8 |
| 11 | Isopropanol | 31.1 |
| 12 | tert.Butylperoxy-2-ethylhexanoate | 3.8 |
| 13 | Isopropanol | 259.7 |
| 14 | Cymel 1130 | 739.4 |
| 15 | CoatOSil 7602[3] | 9.2 |
| 16 | Butanol | 101.7 |
| 17 | Dimethylethanol amine | 28.8 |
| 18 | Triethylamine | 33.0 |
| 19 | Deionized water | 65.7 |
| 20 | Deionized water | 654.3 |
| 21 | Deionized water | 1042.7 |

[1]Propylene glycol methyl ether commercially available from Dow Chemical Co.
[2]Ethylene glycol monobutyl ether commercially available from Dow Chemical Co.
[3]CoatOSil 7602 is a silicone copolymer commercially available from Momentive.

Charges 1 and 2 were added to a flask set up for total reflux with stirring under nitrogen and heated to 100° C. Charges 3-11 were slowly added via addition funnel over 180 minutes and the reaction mixture was then held at 100° C. for an additional 30 minutes. Charges 12-13 were then added dropwise in 3 portions over separate 60-minute intervals. The reaction mixture was then held at 100° C. for 60 minutes. Charges 14-16 were then added and the reaction mixture held at 100° C. for 15 minutes. The product was cooled to 90° C. and charges 17-19 were added and the reaction mixture held for an additional 15 minutes. The resulting mixture was then reverse thinned into charge 20, which was at ambient temperature, and the resulting mixture was held for 30 minutes. Finally, charge 21 was added and the mixture was held for an additional 30 minutes. Final solids were 29.8%. Final molecular weight as determined by GPC ($M_z$) was 120,311 g/mol.

Comparative Example 11: Preparation of a Pigmented Comparative Aqueous Resinous Dispersion of Example 10 and Electrodeposition Thereof A comparative pigmented aqueous resinous dispersion of the comparative addition polymer and curing agent dispersion of Example 10 was prepared as follows:

TABLE 11

| Charge | Material | Amount (g) |
|---|---|---|
| 1 | Dispersion of Addition Polymer of Example 11 | 1735.2 |
| 2 | ACPP2220[1] | 271.4 |
| 3 | Deionized water | 1193.5 |

[1]Commercially available electrocoat pigment paste available through PPG Industries, Inc.

Charge 1 was added to a 1-gallon plastic bucket and agitation was started. Charge 2 was added slowly over 5 minutes. Finally, charge 3 was added over 5 minutes and the resulting mixture stirred for an additional 15 minutes.

After ultrafiltration, the paint was electrodeposited (applied at a voltage of 280V for 90 s duration with a bath temperature of 80° F.) onto a 2024 T3 aluminum substrate and baked in an oven set to a temperature of 250° F. for 60 minutes. Cure testing by the Double Acetone Rub Test Method revealed that the film was not fully cured (20 DAR to metal).

After initial cure testing, 1.5% (on paint solids) Nacure 1051 (acid catalyst based on dinonylnapthalene sulfonic acid available from King Industries) was added as a free species to the paint bath and cure testing was performed again. The film now passed 100 DAR after a 60-minute bake at 250° F. However, the film was left with no adhesion to the substrate, as it did not pass crosshatch adhesion testing performed according to ISO2409.

Comparative Example 12: Preparation of a Comparative Addition Polymer Having Sulfonic Acid and Hydroxyl Functional Groups and Aqueous Resinous Dispersion of the Comparative Addition Polymer and a Curing Agent A comparative addition polymer having sulfonic acid and hydroxyl functional groups, without carbamate functional groups, and an aqueous dispersion of the same with a curing agent was prepared as follows:

TABLE 12

| Charge | Material | Amount (g) |
|---|---|---|
| 1 | Butanol | 55.4 |
| 2 | Methacrylic acid | 25.2 |
| 3 | Styrene | 87.7 |
| 4 | Butyl acrylate | 172.6 |
| 5 | Hydroxyethyl acrylate | 33.7 |
| 6 | t-dodecylmercaptan | 10.4 |
| 7 | Butanol | 26.7 |
| 8 | t-butylperbenzoate | 3.8 |
| 9 | Butanol | 30.6 |
| 10 | 2-Acrylamide-2-methylpropane sulfonic acid (AMPS) | 6.5 |
| 11 | Diisopropanolamine | 4.4 |
| 12 | Butanol | 6.0 |
| 13 | t-butylperbenzoate | 0.9 |
| 14 | Deionized water | 23.3 |
| 15 | Diisopropanolamine | 30.3 |
| 16 | Deionized water | 2.5 |
| 17 | Cymel 1130 | 125.0 |
| 18 | Deionized water | 315.2 |
| 19 | Deionized water | 265.8 |
| 20 | Deionized water | 512.7 |

Charge 1 was added to a flask set up for total reflux with stirring under nitrogen and heated to 115° C. Charges 2-11 (with charges 9-11 premixed) were slowly added via addition funnel over 180 minutes and the resulting mixture was then held at 115° C. for an additional 30 minutes. Charges 12-13 were then added dropwise in 2 portions over separate 60-minute intervals. The reaction mixture was then held for an additional 60 minutes at 115° C. The reaction was then switched to total distillation and 113 g of butanol were distilled off from the reaction mixture under vacuum. The reaction mixture was then cooled to 105° C., charge 14 was added slowly, and then the reaction mixture was cooled to 95° C. Charges 15-16 were then added and the reaction mixture held for 30 minutes. Charge 17 was added and held for an additional 30 minutes. The resulting mixture was then reverse thinned into charge 18, which was at ambient temperature, and the mixture was held for 30 minutes. Charge 19 was then added and the mixture was held for 30 minutes. Finally, charge 20 was added and held for 30 minutes. Final solids were 25.7%. Final molecular weight as determined by GPC ($M_z$) was 19,678 g/mol.

Comparative Example 13: Preparation of a Comparative Pigmented Aqueous Resinous Dispersion of the Aqueous Resinous Dispersion of Example 12 and Electrodeposition Thereof A comparative pigmented aqueous resinous dispersion of the comparative addition polymer and curing agent dispersion of Example 12 was prepared as follows:

TABLE 7

| Charge | Material | Amount (g) |
|---|---|---|
| 1 | Dispersion of Addition Polymer of Example 12 | 1525.0 |
| 2 | ACPP2220[1] | 213.4 |
| 3 | Deionized water | 761.6 |

[1]Commercially available electrocoat pigment paste available through PPG Industries, Inc Charge 1 was added to a 1-gallon plastic bucket and agitation was started. Charge 2 was added slowly over 5 minutes. Finally, charge 3 was added over 5 minutes and the resulting mixture stirred for an additional 15 minutes.

After ultrafiltration, the paint was electrodeposited (applied voltage of 200V for 90 s duration with a bath temperature of 75° F.) onto a 2024 T3 aluminum substrate and baked in an oven set to a temperature of 250° F. for 60 minutes. Cure testing by the Double Acetone Rub Test Method revealed that the film was fully cured (100 DAR). The film also passed crosshatch adhesion testing performed according to ISO 2409.

The film was then immersed in water at a temperature of 90° C. for 24 hours. It was then removed and baked in an oven set to 150° F. for 60 minutes to dehydrate the film. Upon retesting for cure using the Double Acetone Rub Test Method, the film failed to metal after only 50 rubs.

It will be appreciated by skilled artisans that numerous modifications and variations are possible in light of the above disclosure without departing from the broad inventive concepts described and exemplified herein. Accordingly, it is therefore to be understood that the foregoing disclosure is merely illustrative of various exemplary aspects of this application and that numerous modifications and variations can be readily made by skilled artisans which are within the spirit and scope of this application and the accompanying claims.

We claim:

1. A compound of formula I,

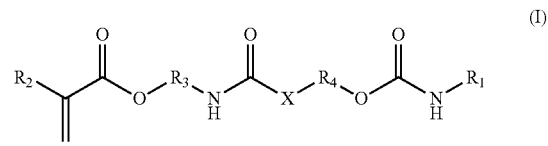

wherein $R_1$ comprises hydrogen or an alkyl group; $R_2$ comprises hydrogen or a methyl group; $R_3$ comprises a divalent organic group; $R_4$ comprises a divalent organic group; and X comprises oxygen, NH, or $N(R_5)$, wherein $R_5$ comprises a monovalent organic group.

2. The compound of claim 1, wherein the compound comprises the structure:

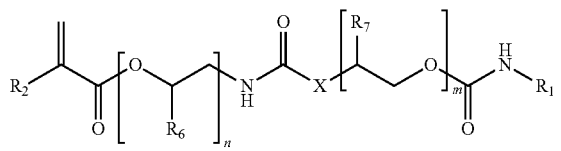

wherein $R_1$ comprises hydrogen or an alkyl group; $R_2$ comprises hydrogen or a methyl group; $R_6$ comprises hydrogen or a methyl group; $R_7$ comprises hydrogen or a methyl group; X comprises oxygen, NH, or $N(R_5)$ wherein $R_5$ comprises a monovalent organic group; m is a positive integer from 1 to 100; and n is a positive integer from 1 to 100.

3. The compound of claim 1, wherein the compound comprises the structure:

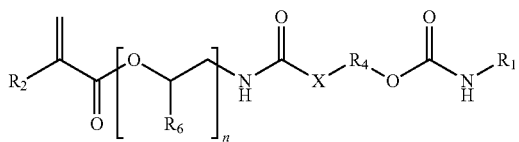

wherein $R_1$ comprises hydrogen or an alkyl group; $R_2$ comprises hydrogen or a methyl group; $R_4$ comprises a divalent organic group; $R_6$ comprises hydrogen or a methyl group; X comprises oxygen, NH, or $N(R_5)$ wherein $R_5$ comprises a monovalent organic group; and n is a positive integer from 1 to 100.

4. The compound of claim 1, wherein the compound comprises the structure:

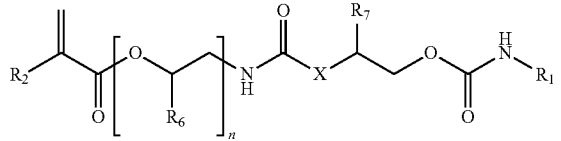

wherein $R_1$ comprises hydrogen or an alkyl group; $R_2$ comprises hydrogen or a methyl group; $R_6$ comprises hydrogen or a methyl group; $R_7$ comprises hydrogen or a methyl group; X comprises oxygen, NH, or $N(R_5)$ wherein $R_5$ comprises a monovalent organic group; and n is a positive integer from 1 to 100.

5. The compound of claim 1, wherein the compound comprises the structure:

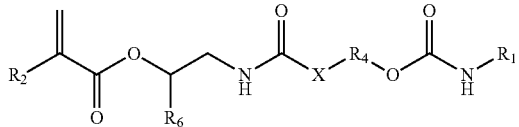

wherein $R_1$ comprises hydrogen or an alkyl group; $R_2$ comprises hydrogen or a methyl group; $R_4$ comprises a divalent organic group; $R_6$ comprises hydrogen or a methyl group; and X comprises oxygen, NH, or $N(R_5)$ wherein $R_5$ comprises a monovalent organic group.

6. The compound of claim 1, wherein the compound comprises the structure:

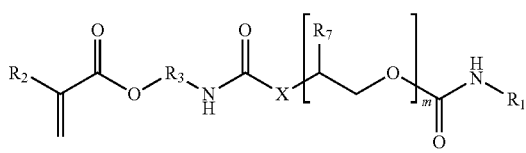

wherein $R_1$ comprises hydrogen or an alkyl group; $R_2$ comprises hydrogen or a methyl group; $R_3$ comprises a divalent organic group; $R_7$ comprises hydrogen or a methyl group; X comprises oxygen, NH, or $N(R_5)$ wherein $R_5$ comprises a monovalent organic group; and m is a positive integer from 1 to 100.

7. The compound of claim 1, wherein the compound comprises the structure:

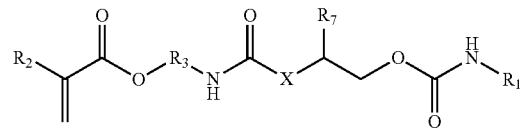

wherein $R_1$ comprises hydrogen or an alkyl group; $R_2$ comprises hydrogen or a methyl group; $R_3$ comprises a divalent organic group; $R_7$ comprises hydrogen or a methyl group; and X comprises oxygen, NH, or $N(R_5)$ wherein $R_5$ comprises a monovalent organic group.

8. The compound of claim 1, wherein the compound comprises the structure:

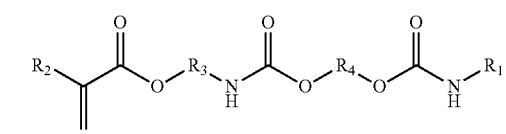

wherein $R_1$ comprises hydrogen or an alkyl group; $R_2$ comprises hydrogen or a methyl group; $R_3$ comprises a divalent organic group; and $R_4$ comprises a divalent organic group.

9. A compound comprising the structure:

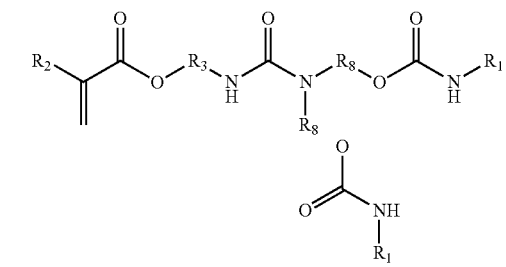

wherein each $R_1$ independently comprises hydrogen, an alkyl group; $R_2$ comprises hydrogen or a methyl group; $R_3$ comprises a divalent organic group; and each $R_8$ independently comprises a divalent organic group.

10. The compound of claim 9, wherein the compound comprises the structure:

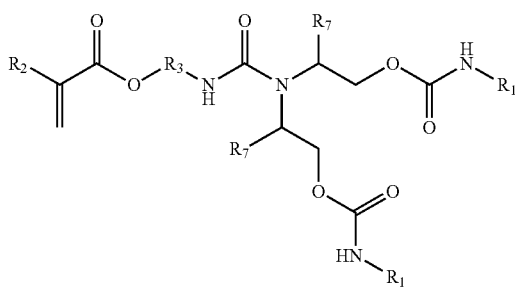

wherein each R₁ independently comprises hydrogen, an alkyl group; R₂ comprises hydrogen or a methyl group; R₃ comprises a divalent organic group; and each R₇ independently comprises hydrogen or a methyl group.

11. The compound of claim 1, wherein the compound comprises the structure:

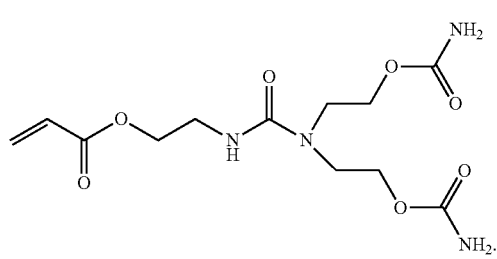 [SMILES: C=CC(=O)OCCNC(=O)N(CCOC(N)=O)CCOC(N)=O]

12. The compound of claim 1, wherein the compound comprises the structure:

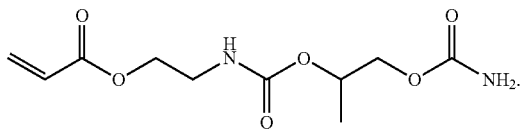 [SMILES: C=CC(=O)OCCNC(=O)OC(C)COC(N)=O]

13. A polymer comprising a pendant carbamate-functional moiety comprising the structure:

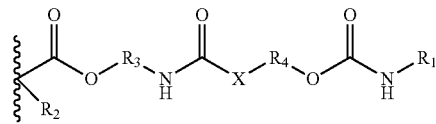

wherein R₁ comprises hydrogen or an alkyl group; R₂ comprises hydrogen or a methyl group; R₃ comprises a divalent organic group; R₄ comprises a divalent organic group; and X comprises oxygen, NH, or N(R₅) wherein R₅ comprises a monovalent organic group.

14. The polymer of claim 13, wherein the polymer comprises the residue of the compound of claim 1.

15. A curable film-forming composition comprising the polymer of claim 13.

16. An aqueous dispersion comprising the polymer of claim 13.

17. A coating comprising the polymer of claim 13.

18. A substrate coated with the curable film-forming composition of claim 15.

19. A substrate coated with the aqueous dispersion of claim 16.

20. A method of preparing the compound of claim 1, wherein X comprises oxygen, the method comprising the step of reacting an isocyanato functional unsaturated monomer of formula II with a hydroxyl functional, carbamate functional monomer according to formula III,

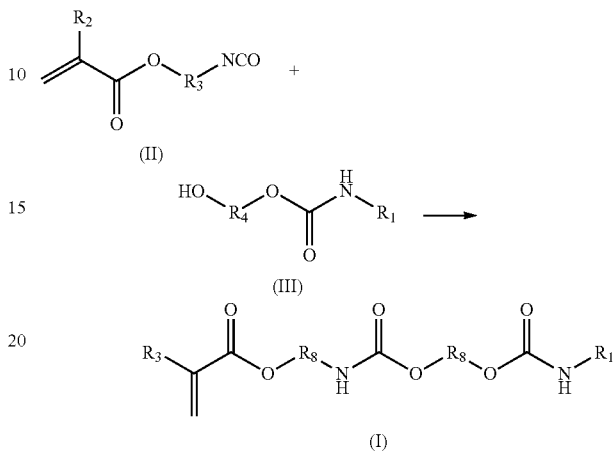

wherein R₁ comprises hydrogen or an alkyl group; R₂ comprises hydrogen or a methyl group; R₃ comprises a divalent organic group; and R₄ comprises a divalent organic group.

21. A method of preparing the compound of claim 1, wherein X comprises N(R₅), the method comprising the steps of (1) reacting an isocyanato functional unsaturated compound of formula II with a dihydroxy alkyl amine compound of formula IV to form a reaction product,

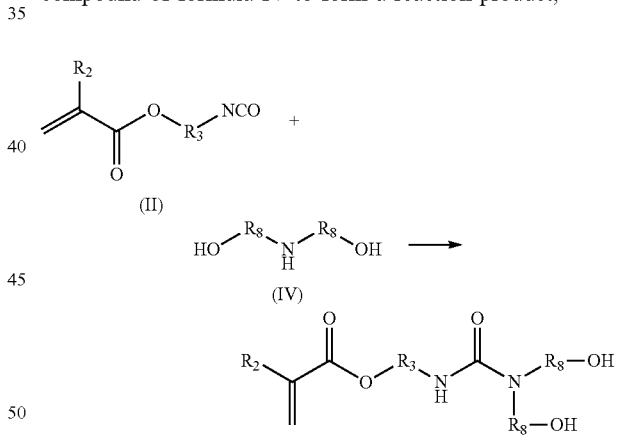

and (2) further reacting the reaction product with a carbamate ester according to formula V,

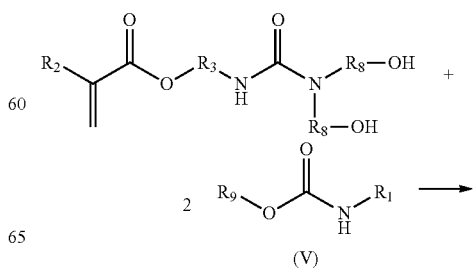

-continued
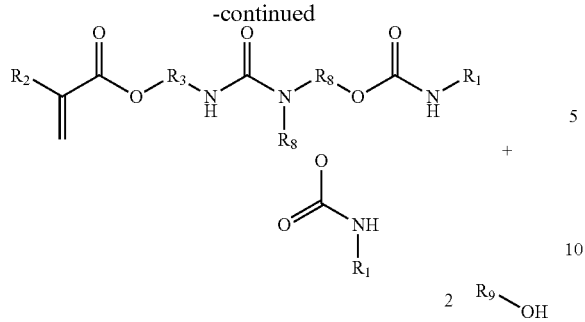
wherein $R_1$ comprises hydrogen or an alkyl group; $R_2$ comprises hydrogen or a methyl group; $R_3$ comprises a divalent organic group; each $R_8$ independently comprises a divalent organic group; and $R_9$ comprises a monovalent organic group.
22. The compound of claim 1, wherein $R_1$ is hydrogen.
* * * * *